US012691266B2

(12) United States Patent
Murray et al.

(10) Patent No.: US 12,691,266 B2
(45) Date of Patent: Jul. 28, 2026

(54) FLEXIBLE SHUNT IMPLANTS

(71) Applicant: EDWARDS LIFESCIENCES CORPORATION, Irvine, CA (US)

(72) Inventors: Daniel James Murray, Orange, CA (US); Eric Jason Noda, Rancho Santa Margarita, CA (US); Linda Thai, Mission Viejo, CA (US); Jonathan Andrew Lam, Anaheim Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 236 days.

(21) Appl. No.: 18/336,265

(22) Filed: Jun. 16, 2023

(65) Prior Publication Data

US 2023/0338028 A1      Oct. 26, 2023

Related U.S. Application Data

(63) Continuation of application No. PCT/US2021/063773, filed on Dec. 16, 2021.

(60) Provisional application No. 63/199,323, filed on Dec. 18, 2020.

(51) Int. Cl.
| | |
|---|---|
| *A61M 27/00* | (2006.01) |
| *A61B 17/00* | (2006.01) |
| *A61B 17/11* | (2006.01) |
| *A61B 17/34* | (2006.01) |

(52) U.S. Cl.
CPC ........... *A61M 27/002* (2013.01); *A61B 17/11* (2013.01); *A61B 17/3415* (2013.01); *A61B 2017/00252* (2013.01); *A61B 2017/003* (2013.01); *A61B 2017/00867* (2013.01); *A61B 2017/1139* (2013.01)

(58) Field of Classification Search
CPC ................. A61M 27/002; A61B 17/11; A61B 2017/00243; A61F 2/86; A61F 2230/0091
See application file for complete search history.

(56) References Cited

U.S. PATENT DOCUMENTS

| | | | |
|---|---|---|---|
| 3,538,917 | A | 11/1970 | Selker |
| 3,675,656 | A | 7/1972 | Hakim |
| 3,730,186 | A | 5/1973 | Edmunds, Jr. et al. |
| 3,853,126 | A | 12/1974 | Schulte |

(Continued)

FOREIGN PATENT DOCUMENTS

| | | |
|---|---|---|
| WO | WO-1997027898 A1 | 8/1997 |
| WO | WO-2017062858 A1 | 4/2017 |

(Continued)

OTHER PUBLICATIONS

Emil Mantini, MD, et al., Title: Congenital Anomalies Involving the Coronary Sinus, Circulation, Journal of the American Heart Association, vol. XXXIII, Feb. 1966, pp. 317-327.

(Continued)

*Primary Examiner* — Leslie R Deak
(74) *Attorney, Agent, or Firm* — Klarquist Sparkman LLP

(57) ABSTRACT

A delivery system comprises a catheter configured to be delivered through a blood flow pathway of a heart and an implant configured to maintain an opening in a tissue wall to allow blood flow through the opening and into the blood flow pathway and be delivered via the catheter. The implant is at least partially composed of a flexible material to allow the implant to bend with the catheter.

34 Claims, 10 Drawing Sheets

(56) References Cited

U.S. PATENT DOCUMENTS

| | | | |
|---|---|---|---|
| 3,882,862 | A | 5/1975 | Berend |
| 3,882,882 | A | 5/1975 | Preisig |
| 3,903,894 | A | 9/1975 | Rosen et al. |
| 4,256,094 | A | 3/1981 | Kapp et al. |
| 4,428,365 | A | 1/1984 | Hakky |
| 4,556,050 | A | 12/1985 | Hodgson et al. |
| 4,578,061 | A | 3/1986 | Lemelson |
| 4,586,501 | A | 5/1986 | Claracq |
| 4,601,718 | A | 7/1986 | Possis et al. |
| 4,655,777 | A | 4/1987 | Dunn et al. |
| 4,708,140 | A | 11/1987 | Baron |
| 4,712,551 | A | 12/1987 | Rayhanabad |
| 4,739,762 | A | 4/1988 | Palmaz |
| 4,762,128 | A | 8/1988 | Rosenbluth |
| 4,774,949 | A | 10/1988 | Fogarty |
| 4,776,337 | A | 10/1988 | Palmaz |
| 4,828,544 | A | 5/1989 | Lane et al. |
| 4,861,336 | A | 8/1989 | Helzel |
| 4,881,939 | A | 11/1989 | Newman |
| 4,946,457 | A | 8/1990 | Elliott |
| 4,950,227 | A | 8/1990 | Savin et al. |
| 4,961,729 | A | 10/1990 | Vaillancourt |
| 4,997,431 | A | 3/1991 | Isner et al. |
| 5,026,377 | A | 6/1991 | Burton et al. |
| 5,054,492 | A | 10/1991 | Scribner et al. |
| 5,106,386 | A | 4/1992 | Isner et al. |
| 5,108,420 | A | 4/1992 | Marks |
| 5,109,420 | A | 4/1992 | Nonaka |
| 5,167,239 | A | 12/1992 | Cohen et al. |
| 5,190,528 | A | 3/1993 | Fonger et al. |
| 5,193,546 | A | 3/1993 | Shaknovich |
| 5,201,757 | A | 4/1993 | Heyn et al. |
| 5,242,397 | A | 9/1993 | Barath et al. |
| 5,242,410 | A | 9/1993 | Melker |
| 5,258,042 | A | 11/1993 | Mehta |
| 5,267,940 | A | 12/1993 | Moulder |
| 5,287,861 | A | 2/1994 | Wilk |
| 5,330,496 | A | 7/1994 | Alferness |
| 5,334,217 | A | 8/1994 | Das |
| 5,345,940 | A | 9/1994 | Seward et al. |
| 5,354,279 | A | 10/1994 | Hofling |
| 5,366,490 | A | 11/1994 | Edwards et al. |
| 5,373,849 | A | 12/1994 | Maroney et al. |
| 5,419,777 | A | 5/1995 | Hofling |
| 5,423,878 | A | 6/1995 | Franz |
| 5,429,634 | A | 7/1995 | Narciso, Jr. |
| 5,431,700 | A | 7/1995 | Sloan |
| 5,443,497 | A | 8/1995 | Venbrux |
| 5,445,600 | A | 8/1995 | Abdulla |
| 5,445,646 | A | 8/1995 | Euteneuer et al. |
| 5,456,284 | A | 10/1995 | Ryan et al. |
| 5,456,712 | A | 10/1995 | Maginot |
| 5,462,523 | A | 10/1995 | Samson et al. |
| 5,464,395 | A | 11/1995 | Faxon et al. |
| 5,491,224 | A | 2/1996 | Bittner et al. |
| 5,496,311 | A | 3/1996 | Abele et al. |
| 5,499,630 | A | 3/1996 | Hiki et al. |
| 5,507,724 | A | 4/1996 | Hofmann et al. |
| 5,507,725 | A | 4/1996 | Savage et al. |
| 5,538,504 | A | 7/1996 | Linden et al. |
| 5,551,954 | A | 9/1996 | Buscemi et al. |
| 5,554,182 | A | 9/1996 | Dinh et al. |
| 5,570,693 | A | 11/1996 | Jang et al. |
| 5,571,086 | A | 11/1996 | Kaplan et al. |
| 5,571,151 | A | 11/1996 | Gregory |
| 5,588,960 | A | 12/1996 | Edwards et al. |
| 5,597,378 | A | 1/1997 | Jervis |
| 5,599,300 | A | 2/1997 | Weaver et al. |
| 5,614,204 | A | 3/1997 | Cochrum |
| 5,628,784 | A | 5/1997 | Strecker |
| 5,661,133 | A | 8/1997 | Leiden et al. |
| 5,662,609 | A | 9/1997 | Slepian |
| 5,662,711 | A | 9/1997 | Douglas |
| 5,665,077 | A | 9/1997 | Rosen et al. |
| 5,669,880 | A | 9/1997 | Solar |
| 5,682,906 | A | 11/1997 | Sterman et al. |
| 5,690,670 | A | 11/1997 | Davidson |
| 5,693,029 | A | 12/1997 | Leonhardt |
| 5,704,361 | A | 1/1998 | Seward et al. |
| 5,704,926 | A | 1/1998 | Sutton |
| 5,713,363 | A | 2/1998 | Seward et al. |
| 5,713,853 | A | 2/1998 | Clark et al. |
| 5,718,725 | A | 2/1998 | Sterman et al. |
| 5,724,975 | A | 3/1998 | Negus et al. |
| 5,724,977 | A | 3/1998 | Yock et al. |
| 5,728,123 | A | 3/1998 | Lemelson et al. |
| 5,735,847 | A | 4/1998 | Gough et al. |
| 5,738,658 | A | 4/1998 | Maus et al. |
| 5,743,874 | A | 4/1998 | Fischell et al. |
| 5,755,682 | A | 5/1998 | Knudson et al. |
| 5,756,696 | A | 5/1998 | Gray et al. |
| 5,771,895 | A | 6/1998 | Slager |
| 5,772,629 | A | 6/1998 | Kaplan |
| 5,772,632 | A | 6/1998 | Forman |
| 5,807,258 | A | 9/1998 | Cimochowski et al. |
| 5,807,306 | A | 9/1998 | Shapland et al. |
| 5,810,780 | A | 9/1998 | Brimhall et al. |
| 5,814,005 | A | 9/1998 | Barra et al. |
| 5,827,216 | A | 10/1998 | Igo et al. |
| 5,830,222 | A | 11/1998 | Makower |
| 5,830,224 | A | 11/1998 | Cohn et al. |
| 5,836,913 | A | 11/1998 | Orth et al. |
| 5,843,090 | A | 12/1998 | Schuetz |
| 5,843,170 | A | 12/1998 | Ahn |
| 5,944,738 | A | 8/1999 | Amplatz et al. |
| 5,951,569 | A | 9/1999 | Tuckey et al. |
| 5,989,280 | A | 11/1999 | Euteneuer et al. |
| 6,019,788 | A | 2/2000 | Butters et al. |
| 6,042,589 | A | 3/2000 | Marianne |
| 6,053,891 | A | 4/2000 | DeCampli |
| 6,068,638 | A | 5/2000 | Makower |
| 6,081,738 | A | 6/2000 | Hinohara et al. |
| 6,086,553 | A | 7/2000 | Akbik |
| 6,092,526 | A | 7/2000 | LaFontaine et al. |
| 6,095,878 | A | 8/2000 | Van Balen |
| 6,099,542 | A | 8/2000 | Cohn et al. |
| 6,113,612 | A | 9/2000 | Swanson et al. |
| 6,120,494 | A | 9/2000 | Jonkman |
| 6,120,522 | A | 9/2000 | Vrba et al. |
| 6,120,534 | A | 9/2000 | Ruiz |
| 6,152,937 | A | 11/2000 | Peterson et al. |
| 6,159,225 | A | 12/2000 | Makower |
| 6,165,185 | A | 12/2000 | Shennib et al. |
| 6,168,620 | B1 | 1/2001 | Kerr |
| 6,168,820 | B1 | 1/2001 | Garwood et al. |
| 6,174,681 | B1 | 1/2001 | Halling et al. |
| 6,190,353 | B1 | 2/2001 | Makower et al. |
| 6,193,734 | B1 | 2/2001 | Bolduc et al. |
| 6,196,230 | B1 | 3/2001 | Hall et al. |
| 6,231,587 | B1 | 5/2001 | Makower |
| 6,241,743 | B1 | 6/2001 | Levin et al. |
| 6,248,117 | B1 | 6/2001 | Blatter |
| 6,251,116 | B1 | 6/2001 | Shennib et al. |
| 6,254,631 | B1 | 7/2001 | Thompson |
| 6,280,412 | B1 | 8/2001 | Pederson, Jr. et al. |
| 6,283,951 | B1 | 9/2001 | Flaherty et al. |
| 6,287,332 | B1 | 9/2001 | Bolz et al. |
| 6,290,728 | B1 | 9/2001 | Phelps et al. |
| 6,302,875 | B1 | 10/2001 | Makower et al. |
| 6,302,892 | B1 | 10/2001 | Wilk |
| 6,302,905 | B1 | 10/2001 | Goldsteen et al. |
| 6,309,415 | B1 | 10/2001 | Pulnev et al. |
| 6,315,752 | B1 | 11/2001 | DiMatteo |
| 6,325,798 | B1 | 12/2001 | Edwards et al. |
| 6,361,545 | B1 | 3/2002 | Macoviak et al. |
| 6,375,615 | B1 | 4/2002 | Flaherty et al. |
| 6,376,188 | B1 | 4/2002 | Halling et al. |
| 6,387,116 | B1 | 5/2002 | McKenzie et al. |
| 6,387,119 | B2 | 5/2002 | Wolf et al. |
| 6,391,036 | B1 | 5/2002 | Berg et al. |
| 6,402,767 | B1 | 6/2002 | Nash et al. |
| 6,409,751 | B1 | 6/2002 | Hall et al. |
| 6,443,158 | B1 | 9/2002 | LaFontaine et al. |
| 6,451,048 | B1 | 9/2002 | Berg et al. |

(56)     References Cited

U.S. PATENT DOCUMENTS

| | | | |
|---|---|---|---|
| 6,458,140 B2 | 10/2002 | Akin et al. |
| 6,464,665 B1 | 10/2002 | Heuser |
| 6,468,303 B1 | 10/2002 | Amplatz et al. |
| 6,475,226 B1 | 11/2002 | Belef et al. |
| 6,494,889 B1 | 12/2002 | Fleischman et al. |
| 6,503,247 B2 | 1/2003 | Swartz et al. |
| 6,506,201 B2 | 1/2003 | Di Caprio et al. |
| 6,508,824 B1 | 1/2003 | Flaherty et al. |
| 6,561,998 B1 | 5/2003 | Roth et al. |
| 6,562,066 B1 | 5/2003 | Martin |
| 6,565,542 B2 | 5/2003 | Kumar et al. |
| 6,575,168 B2 | 6/2003 | LaFontaine et al. |
| 6,579,311 B1 | 6/2003 | Makower |
| 6,589,251 B2 | 7/2003 | Yee et al. |
| 6,595,941 B1 | 7/2003 | Blatter |
| 6,599,303 B1 | 7/2003 | Peterson et al. |
| 6,602,241 B2 | 8/2003 | Makower et al. |
| 6,613,074 B1 | 9/2003 | Mitelberg et al. |
| 6,616,624 B1 | 9/2003 | Kieval |
| 6,616,675 B1 | 9/2003 | Evard et al. |
| 6,620,202 B2 | 9/2003 | Bottcher et al. |
| 6,623,494 B1 | 9/2003 | Blatter |
| 6,626,920 B2 | 9/2003 | Whayne |
| 6,638,293 B1 | 10/2003 | Makower et al. |
| 6,660,024 B1 | 12/2003 | Flaherty et al. |
| 6,669,709 B1 | 12/2003 | Cohn et al. |
| 6,685,648 B2 | 2/2004 | Flaherty et al. |
| 6,692,482 B2 | 2/2004 | Heller et al. |
| 6,695,878 B2 | 2/2004 | McGuckin, Jr. et al. |
| 6,699,256 B1 | 3/2004 | Logan et al. |
| 6,702,828 B2 | 3/2004 | Whayne |
| 6,709,414 B2 | 3/2004 | Weitzel et al. |
| 6,709,444 B1 | 3/2004 | Makower |
| 6,712,836 B1 | 3/2004 | Berg et al. |
| 6,719,804 B2 | 4/2004 | St. Pierre |
| 6,726,659 B1 | 4/2004 | Stocking et al. |
| 6,726,677 B1 | 4/2004 | Flaherty et al. |
| 6,736,825 B2 | 5/2004 | Blatter et al. |
| 6,740,426 B2 | 5/2004 | Kawachi et al. |
| 6,743,244 B2 | 6/2004 | Blatter et al. |
| 6,743,259 B2 | 6/2004 | Ginn |
| 6,746,426 B1 | 6/2004 | Flaherty et al. |
| 6,746,464 B1 | 6/2004 | Makower |
| 6,748,484 B1 | 6/2004 | Henderson et al. |
| 6,758,854 B1 | 7/2004 | Butler et al. |
| 6,776,785 B1 | 8/2004 | Yencho et al. |
| 6,797,083 B2 | 9/2004 | Peterson |
| 6,802,858 B2 | 10/2004 | Gambale et al. |
| 6,805,706 B2 | 10/2004 | Solovay et al. |
| 6,808,498 B2 | 10/2004 | Laroya et al. |
| 6,827,698 B1 | 12/2004 | Kleinekofort |
| 6,847,348 B2 | 1/2005 | Rojewski |
| 6,854,172 B2 | 2/2005 | Kaese et al. |
| 6,858,035 B2 | 2/2005 | Whayne |
| 6,869,437 B1 | 3/2005 | Hausen et al. |
| 6,893,413 B2 | 5/2005 | Martin |
| 6,913,600 B2 | 7/2005 | Valley et al. |
| 6,913,607 B2 | 7/2005 | Ainsworth et al. |
| 6,915,154 B1 | 7/2005 | Docherty et al. |
| 6,926,690 B2 | 8/2005 | Renati |
| 6,929,011 B2 | 8/2005 | Knudson et al. |
| 6,953,481 B2 | 10/2005 | Phelps et al. |
| 6,972,023 B2 | 12/2005 | Whayne et al. |
| 6,979,351 B2 | 12/2005 | Forsell et al. |
| 6,985,774 B2 | 1/2006 | Kieval et al. |
| 7,002,491 B2 | 2/2006 | Robbins |
| 7,004,175 B2 | 2/2006 | LaFontaine et al. |
| 7,008,397 B2 | 3/2006 | Tweden et al. |
| 7,011,094 B2 | 3/2006 | Rapacki et al. |
| 7,011,678 B2 | 3/2006 | Tenerz et al. |
| 7,025,741 B2 | 4/2006 | Cull |
| 7,025,746 B2 | 4/2006 | Tal |
| 7,037,329 B2 | 5/2006 | Martin |
| 7,056,294 B2 | 6/2006 | Khairkhahan et al. |
| 7,056,320 B2 | 6/2006 | Utley et al. |
| 7,056,325 B1 | 6/2006 | Makower et al. |
| 7,056,326 B2 | 6/2006 | Bolduc et al. |
| 7,077,860 B2 | 7/2006 | Yan et al. |
| 7,083,631 B2 | 8/2006 | Houser et al. |
| 7,108,701 B2 | 9/2006 | Evens et al. |
| 7,115,136 B2 | 10/2006 | Park et al. |
| 7,118,546 B2 | 10/2006 | Blatter |
| 7,128,750 B1 | 10/2006 | Stergiopulos |
| 7,134,438 B2 | 11/2006 | Makower et al. |
| 7,175,644 B2 | 2/2007 | Cooper et al. |
| 7,182,771 B1 | 2/2007 | Houser et al. |
| 7,235,095 B2 | 6/2007 | Haverkost et al. |
| 7,294,115 B1 | 11/2007 | Wilk |
| 7,303,569 B2 | 12/2007 | Yencho et al. |
| 7,316,706 B2 | 1/2008 | Bloom et al. |
| 7,317,951 B2 | 1/2008 | Schneider et al. |
| 7,318,804 B2 | 1/2008 | Weitzel et al. |
| 7,326,221 B2 | 2/2008 | Sakamoto et al. |
| 7,331,985 B2 | 2/2008 | Thompson et al. |
| 7,335,220 B2 | 2/2008 | Khosravi et al. |
| 7,351,247 B2 | 4/2008 | Kupiecki et al. |
| 7,361,181 B2 | 4/2008 | Hindrichs et al. |
| 7,374,567 B2 | 5/2008 | Heuser |
| 7,387,636 B2 | 6/2008 | Cohn et al. |
| D581,054 S | 11/2008 | Moore |
| 7,462,162 B2 | 12/2008 | Phan et al. |
| 7,476,200 B2 | 1/2009 | Tal |
| 7,485,104 B2 | 2/2009 | Kieval |
| 7,530,963 B2 | 5/2009 | Albright |
| 7,563,277 B2 | 7/2009 | Case et al. |
| 7,623,926 B2 | 11/2009 | Rossing et al. |
| 7,625,593 B2 | 12/2009 | Mandrusov et al. |
| 7,628,768 B2 | 12/2009 | Faul et al. |
| D612,499 S | 3/2010 | Ondracek et al. |
| 7,691,110 B2 | 4/2010 | Secrest et al. |
| 7,699,863 B2 | 4/2010 | Marco et al. |
| 7,722,549 B2 | 5/2010 | Nakao |
| 7,722,567 B2 | 5/2010 | Tal |
| 7,722,665 B2 | 5/2010 | Anwar et al. |
| 7,729,738 B2 | 6/2010 | Flaherty et al. |
| 7,744,621 B2 | 6/2010 | Paul et al. |
| 7,780,686 B2 | 8/2010 | Park et al. |
| 7,794,495 B2 | 9/2010 | Gale et al. |
| 7,807,191 B2 | 10/2010 | Iyer et al. |
| 7,815,590 B2 | 10/2010 | Cooper |
| 7,815,656 B2 | 10/2010 | Rust et al. |
| 7,815,852 B2 | 10/2010 | Sternby |
| 7,828,814 B2 | 11/2010 | Brenneman et al. |
| 7,846,179 B2 | 12/2010 | Belef et al. |
| 7,846,194 B2 | 12/2010 | Hartley et al. |
| 7,850,705 B2 | 12/2010 | Bachinski et al. |
| 7,867,547 B2 | 1/2011 | Tochterman et al. |
| 7,879,367 B2 | 2/2011 | Heublein et al. |
| 7,892,246 B2 | 2/2011 | Akin et al. |
| 7,892,247 B2 | 2/2011 | Conston et al. |
| 7,923,022 B2 | 4/2011 | Wang et al. |
| 7,951,194 B2 | 5/2011 | Gueriguian et al. |
| 7,959,603 B2 | 6/2011 | Wahr et al. |
| 7,964,210 B2 | 6/2011 | Wang et al. |
| 7,967,769 B2 | 6/2011 | Faul et al. |
| 7,972,346 B2 | 7/2011 | Bachmann et al. |
| 8,002,821 B2 | 8/2011 | Stinson |
| 8,016,782 B2 | 9/2011 | Brenneman et al. |
| 8,029,470 B2 | 10/2011 | Whiting et al. |
| 8,048,150 B2 | 11/2011 | Weber et al. |
| 8,052,751 B2 | 11/2011 | Aklog et al. |
| 8,057,534 B2 | 11/2011 | Boismier et al. |
| 8,070,708 B2 | 12/2011 | Rottenberg et al. |
| 8,088,171 B2 | 1/2012 | Brenneman |
| 8,089,029 B2 | 1/2012 | Flanagan |
| 8,091,556 B2 | 1/2012 | Keren et al. |
| 8,128,689 B2 | 3/2012 | Weber et al. |
| 8,152,773 B2 | 4/2012 | Albrecht et al. |
| 8,182,527 B2 | 5/2012 | Llanos et al. |
| 8,187,217 B2 | 5/2012 | Renati et al. |
| 8,214,015 B2 | 7/2012 | Macaulay et al. |
| 8,221,495 B2 | 7/2012 | Shrivastava et al. |
| 8,226,592 B2 | 7/2012 | Brenneman et al. |
| D665,500 S | 8/2012 | Martin et al. |

(56) References Cited

U.S. PATENT DOCUMENTS

| | | |
|---|---|---|
| 8,235,933 B2 | 8/2012 | Keren et al. |
| 8,236,014 B2 | 8/2012 | Brenneman et al. |
| 8,273,095 B2 | 9/2012 | Brenneman et al. |
| 8,282,591 B2 | 10/2012 | Khan et al. |
| 8,308,682 B2 | 11/2012 | Kramer et al. |
| 8,328,751 B2 | 12/2012 | Keren et al. |
| 8,357,193 B2 | 1/2013 | Phan et al. |
| 8,376,979 B2 | 2/2013 | Kapadia |
| 8,382,697 B2 | 2/2013 | Brenneman et al. |
| D679,015 S | 3/2013 | Nakaji |
| 8,409,167 B2 | 4/2013 | Roschak |
| 8,500,697 B2 | 8/2013 | Kurth et al. |
| 8,506,984 B2 | 8/2013 | Cook et al. |
| 8,518,062 B2 | 8/2013 | Cole et al. |
| 8,518,662 B2 | 8/2013 | Ritzen et al. |
| 8,545,552 B2 | 10/2013 | Garrison et al. |
| 8,574,185 B2 | 11/2013 | Faul et al. |
| 8,641,724 B2 | 2/2014 | Brenneman et al. |
| 8,641,747 B2 | 2/2014 | Brenneman et al. |
| 8,657,790 B2 | 2/2014 | Tal et al. |
| 8,696,611 B2 | 4/2014 | Nitzan et al. |
| D705,427 S | 5/2014 | Jagger et al. |
| 8,734,472 B2 | 5/2014 | Brenneman et al. |
| 8,768,487 B2 | 7/2014 | Farnan et al. |
| 8,784,860 B2 | 7/2014 | Falotico et al. |
| 8,882,830 B2 | 11/2014 | Cartledge et al. |
| 8,920,449 B2 | 12/2014 | Wilkinson |
| 8,926,545 B2 | 1/2015 | Brenneman et al. |
| 8,932,341 B2 | 1/2015 | Brenneman |
| D723,166 S | 2/2015 | Igaki et al. |
| 8,951,276 B2 | 2/2015 | Kellerman et al. |
| 9,005,155 B2 | 4/2015 | Sugimoto |
| 9,011,362 B2 | 4/2015 | Brenneman et al. |
| 9,023,097 B2 | 5/2015 | Brenneman et al. |
| 9,044,588 B2 | 6/2015 | Conn |
| 9,061,115 B2 | 6/2015 | Ward et al. |
| 9,067,050 B2 | 6/2015 | Gallagher et al. |
| 9,179,916 B2 | 11/2015 | Brenneman et al. |
| 9,198,756 B2 | 12/2015 | Aklog et al. |
| 9,232,997 B2 | 1/2016 | Sugimoto et al. |
| 9,277,995 B2 | 3/2016 | Celermajer et al. |
| 9,345,485 B2 | 5/2016 | Dakin et al. |
| 9,439,746 B2 | 9/2016 | Bell et al. |
| 9,456,812 B2 | 10/2016 | Finch et al. |
| 9,468,441 B2 | 10/2016 | Brenneman |
| 9,510,832 B2 | 12/2016 | Brenneman |
| 9,533,128 B2 | 1/2017 | Kramer et al. |
| 9,550,022 B2 | 1/2017 | Brenneman et al. |
| 9,649,480 B2 | 5/2017 | Sugimoto et al. |
| 9,669,148 B2 | 6/2017 | Brenneman et al. |
| 9,681,948 B2 | 6/2017 | Levi et al. |
| 9,693,800 B2 | 7/2017 | Aman et al. |
| 9,706,997 B2 | 7/2017 | Brenneman |
| 9,724,499 B2 | 8/2017 | Rottenberg et al. |
| 9,775,636 B2 | 10/2017 | Fazio et al. |
| 9,789,294 B2 | 10/2017 | Taft et al. |
| 9,801,653 B2 | 10/2017 | Kellerman et al. |
| 9,814,483 B2 | 11/2017 | Vardi |
| 9,827,404 B2 | 11/2017 | Nance et al. |
| 9,839,517 B2 | 12/2017 | Centola et al. |
| 9,872,981 B2 | 1/2018 | Sparks et al. |
| 9,888,926 B2 | 2/2018 | Phan et al. |
| 9,937,036 B2 | 4/2018 | Sugimoto et al. |
| 9,980,815 B2 | 5/2018 | Nitzan et al. |
| 10,039,905 B1 | 8/2018 | Taft et al. |
| 10,076,403 B1 | 9/2018 | Eigler et al. |
| 10,098,643 B2 | 10/2018 | Brenneman |
| 10,111,998 B2 | 10/2018 | Brenneman et al. |
| 10,130,371 B2 | 11/2018 | Dehdashtian et al. |
| 10,232,098 B2 | 3/2019 | Brenneman et al. |
| 10,272,230 B2 | 4/2019 | Malek et al. |
| 10,292,690 B2 | 5/2019 | Celermajer et al. |
| 10,327,746 B2 | 6/2019 | Glimsdale et al. |
| 10,413,284 B2 | 9/2019 | McNamara et al. |
| 10,426,482 B2 | 10/2019 | Rafiee et al. |
| 10,426,497 B2 | 10/2019 | Chou et al. |
| 10,433,851 B2 | 10/2019 | Adams et al. |
| 10,456,259 B2 | 10/2019 | Subramanian et al. |
| 10,543,113 B2 | 1/2020 | Vong et al. |
| 10,561,423 B2 | 2/2020 | Sharma |
| 10,565,835 B2 | 2/2020 | Harrington et al. |
| 10,568,751 B2 | 2/2020 | McNamara |
| 10,595,999 B2 | 3/2020 | Vettukattil et al. |
| 10,709,451 B2 | 7/2020 | Gronberg et al. |
| 10,751,057 B2 | 8/2020 | Brenneman et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,731 B2 | 2/2021 | Bishop et al. |
| 10,925,756 B2 | 2/2021 | Perszyk |
| 10,940,296 B2 | 3/2021 | Keren |
| 11,135,054 B2 | 10/2021 | Nitzan et al. |
| 11,135,410 B2 | 10/2021 | Finch et al. |
| 11,166,705 B2 | 11/2021 | McNamara et al. |
| 11,234,702 B1 | 2/2022 | Eigler et al. |
| 11,291,807 B2 | 4/2022 | Eigler et al. |
| 11,298,117 B2 | 4/2022 | Hariton et al. |
| 11,304,698 B2 | 4/2022 | Sharma |
| 11,395,644 B2 | 7/2022 | Alanbaei |
| 11,420,034 B2 | 8/2022 | Solomon et al. |
| 2001/0000041 A1 | 3/2001 | Selmon et al. |
| 2001/0003985 A1 | 6/2001 | Lafontaine et al. |
| 2001/0004683 A1 | 6/2001 | Gambale et al. |
| 2001/0010007 A1 | 7/2001 | Bachinski et al. |
| 2001/0014790 A1 | 8/2001 | Heller et al. |
| 2001/0016725 A1 | 8/2001 | Valley et al. |
| 2001/0016753 A1 | 8/2001 | Caprio et al. |
| 2001/0021849 A1 | 9/2001 | Swartz et al. |
| 2001/0025643 A1 | 10/2001 | Foley |
| 2001/0034547 A1 | 10/2001 | Hall et al. |
| 2001/0037141 A1 | 11/2001 | Yee et al. |
| 2001/0041931 A1 | 11/2001 | Goldsteen et al. |
| 2001/0044631 A1 | 11/2001 | Akin et al. |
| 2001/0045698 A1 | 11/2001 | Lo |
| 2002/0002349 A1 | 1/2002 | Flaherty et al. |
| 2002/0002401 A1 | 1/2002 | McGuckin et al. |
| 2002/0004060 A1 | 1/2002 | Heublein et al. |
| 2002/0013616 A1 | 1/2002 | Carter et al. |
| 2002/0029079 A1 | 3/2002 | Kim et al. |
| 2002/0042623 A1 | 4/2002 | Blatter et al. |
| 2002/0049486 A1 | 4/2002 | Knudson et al. |
| 2002/0058897 A1 | 5/2002 | Renati |
| 2002/0058955 A1 | 5/2002 | Blatter et al. |
| 2002/0062146 A1 | 5/2002 | Makower et al. |
| 2002/0077566 A1 | 6/2002 | Laroya et al. |
| 2002/0111620 A1 | 8/2002 | Cooper et al. |
| 2002/0135561 A1 | 9/2002 | Rojewski |
| 2002/0138087 A1 | 9/2002 | Shennib et al. |
| 2002/0143389 A1 | 10/2002 | St. Pierre |
| 2002/0165561 A1 | 11/2002 | Ainsworth et al. |
| 2002/0169377 A1 | 11/2002 | Khairkhahan et al. |
| 2002/0169466 A1 | 11/2002 | Peterson et al. |
| 2002/0173742 A1 | 11/2002 | Keren et al. |
| 2002/0189727 A1 | 12/2002 | Peterson |
| 2002/0193751 A1 | 12/2002 | Theeuwes et al. |
| 2002/0198501 A1 | 12/2002 | Kumar et al. |
| 2003/0009182 A1 | 1/2003 | Whayne |
| 2003/0009183 A1 | 1/2003 | Whayne |
| 2003/0014061 A1 | 1/2003 | Houser et al. |
| 2003/0017150 A1 | 1/2003 | Torphy |
| 2003/0024527 A1 | 2/2003 | Ginn |
| 2003/0060858 A1 | 3/2003 | Kieval et al. |
| 2003/0060876 A1 | 3/2003 | Loshakove et al. |
| 2003/0065345 A1 | 4/2003 | Weadock |
| 2003/0065346 A1 | 4/2003 | Evens et al. |
| 2003/0074082 A1 | 4/2003 | Bottcher et al. |
| 2003/0078562 A1 | 4/2003 | Makower et al. |
| 2003/0088256 A1 | 5/2003 | Conston et al. |
| 2003/0093095 A1 | 5/2003 | Whayne et al. |
| 2003/0100920 A1 | 5/2003 | Akin et al. |
| 2003/0120292 A1 | 6/2003 | Park et al. |
| 2003/0130611 A1 | 7/2003 | Martin |
| 2003/0130719 A1 | 7/2003 | Martin |
| 2003/0153874 A1 | 8/2003 | Tal |

(56)            References Cited

U.S. PATENT DOCUMENTS

| | | |
|---|---|---|
| 2003/0158509 A1 | 8/2003 | Tweden et al. |
| 2003/0163188 A1 | 8/2003 | Haverkost et al. |
| 2003/0167030 A1 | 9/2003 | Weitzel et al. |
| 2003/0167064 A1 | 9/2003 | Whayne |
| 2003/0181928 A1 | 9/2003 | Vidlund et al. |
| 2003/0187499 A1 | 10/2003 | Swanson et al. |
| 2003/0195457 A1 | 10/2003 | LaFontaine et al. |
| 2003/0199806 A1 | 10/2003 | Kieval |
| 2003/0206123 A1 | 11/2003 | Robbins |
| 2003/0212418 A1 | 11/2003 | Yencho et al. |
| 2003/0221307 A1 | 12/2003 | Kaese et al. |
| 2003/0225425 A1 | 12/2003 | Kupiecki et al. |
| 2004/0019315 A1 | 1/2004 | Blatter |
| 2004/0059280 A1 | 3/2004 | Makower et al. |
| 2004/0060563 A1 | 4/2004 | Rapacki et al. |
| 2004/0064081 A1 | 4/2004 | Stanish |
| 2004/0068279 A1 | 4/2004 | Hindrichs et al. |
| 2004/0071861 A1 | 4/2004 | Mandrusov et al. |
| 2004/0077990 A1 | 4/2004 | Knudson et al. |
| 2004/0087984 A1 | 5/2004 | Kupiecki et al. |
| 2004/0087997 A1 | 5/2004 | Brenneman |
| 2004/0092879 A1 | 5/2004 | Kraus et al. |
| 2004/0098105 A1 | 5/2004 | Stinson et al. |
| 2004/0098113 A1 | 5/2004 | Forsell et al. |
| 2004/0106980 A1 | 6/2004 | Solovay et al. |
| 2004/0133197 A1 | 7/2004 | Utley et al. |
| 2004/0158143 A1 | 8/2004 | Flaherty et al. |
| 2004/0197409 A1 | 10/2004 | Iyer et al. |
| 2004/0211433 A1 | 10/2004 | Albright |
| 2004/0215168 A1 | 10/2004 | Verrier et al. |
| 2004/0215220 A1 | 10/2004 | Dolan et al. |
| 2004/0215323 A1 | 10/2004 | Stiger |
| 2004/0220598 A1 | 11/2004 | Bolduc et al. |
| 2004/0230156 A1 | 11/2004 | Schreck et al. |
| 2004/0236360 A1 | 11/2004 | Cohn et al. |
| 2004/0236417 A1 | 11/2004 | Yan et al. |
| 2004/0243154 A1 | 12/2004 | Berg et al. |
| 2004/0249334 A1 | 12/2004 | Cull |
| 2004/0249335 A1 | 12/2004 | Faul et al. |
| 2004/0254616 A1 | 12/2004 | Rossing et al. |
| 2004/0260317 A1 | 12/2004 | Bloom et al. |
| 2004/0260318 A1 | 12/2004 | Hunter et al. |
| 2005/0004505 A1 | 1/2005 | Phelps et al. |
| 2005/0004663 A1 | 1/2005 | Llanos et al. |
| 2005/0010279 A1 | 1/2005 | Tenerz et al. |
| 2005/0021085 A1 | 1/2005 | Abrams et al. |
| 2005/0038501 A1 | 2/2005 | Moore et al. |
| 2005/0043708 A1 | 2/2005 | Gleeson et al. |
| 2005/0043752 A1 | 2/2005 | Phan et al. |
| 2005/0049675 A1 | 3/2005 | Wallace |
| 2005/0056292 A1 | 3/2005 | Cooper |
| 2005/0060041 A1 | 3/2005 | Phan et al. |
| 2005/0065589 A1 | 3/2005 | Schneider et al. |
| 2005/0075655 A1 | 4/2005 | Bumbalough et al. |
| 2005/0075656 A1 | 4/2005 | Beaupre |
| 2005/0082226 A1 | 4/2005 | Bene et al. |
| 2005/0107723 A1 | 5/2005 | Wehman et al. |
| 2005/0107733 A1 | 5/2005 | Faul et al. |
| 2005/0124892 A1 | 6/2005 | Weitzel et al. |
| 2005/0148923 A1 | 7/2005 | Sternby |
| 2005/0149096 A1 | 7/2005 | Hilal et al. |
| 2005/0165344 A1 | 7/2005 | Dobak |
| 2005/0215938 A1 | 9/2005 | Khan et al. |
| 2005/0228402 A1 | 10/2005 | Hofmann |
| 2005/0249770 A1 | 11/2005 | Hunter |
| 2005/0249776 A1 | 11/2005 | Chen et al. |
| 2005/0267490 A1 | 12/2005 | Secrest et al. |
| 2005/0272806 A1 | 12/2005 | Falotico et al. |
| 2005/0277964 A1 | 12/2005 | Brenneman et al. |
| 2005/0277965 A1 | 12/2005 | Brenneman et al. |
| 2005/0277967 A1 | 12/2005 | Brenneman et al. |
| 2005/0278013 A1 | 12/2005 | Rust et al. |
| 2005/0288688 A1 | 12/2005 | Sakamoto et al. |
| 2006/0024359 A1 | 2/2006 | Walker et al. |
| 2006/0034466 A1 | 2/2006 | Form et al. |
| 2006/0047337 A1 | 3/2006 | Brenneman |
| 2006/0074398 A1 | 4/2006 | Whiting et al. |
| 2006/0099238 A1 | 5/2006 | Khosravi et al. |
| 2006/0111704 A1 | 5/2006 | Brenneman et al. |
| 2006/0116605 A1 | 6/2006 | Nakao |
| 2006/0116625 A1 | 6/2006 | Renati et al. |
| 2006/0129083 A1 | 6/2006 | Brenneman et al. |
| 2006/0129100 A1 | 6/2006 | Tal |
| 2006/0130591 A1 | 6/2006 | Perkins |
| 2006/0130767 A1 | 6/2006 | Herchen |
| 2006/0135984 A1 | 6/2006 | Kramer et al. |
| 2006/0136036 A1 | 6/2006 | Thompson et al. |
| 2006/0161197 A1 | 7/2006 | Paul et al. |
| 2006/0182536 A1 | 8/2006 | Rice et al. |
| 2006/0184011 A1 | 8/2006 | Macaulay et al. |
| 2006/0198869 A1 | 9/2006 | Furst et al. |
| 2006/0206029 A1 | 9/2006 | Yair |
| 2006/0206123 A1 | 9/2006 | Brenneman |
| 2006/0241342 A1 | 10/2006 | Macaulay et al. |
| 2006/0264801 A1 | 11/2006 | Bolling et al. |
| 2006/0264986 A1 | 11/2006 | Park et al. |
| 2006/0270963 A1 | 11/2006 | Bolling et al. |
| 2006/0271196 A1 | 11/2006 | Saal et al. |
| 2006/0282106 A1 | 12/2006 | Cole et al. |
| 2006/0287704 A1 | 12/2006 | Hartley et al. |
| 2006/0293701 A1 | 12/2006 | Ainsworth et al. |
| 2007/0049970 A1 | 3/2007 | Belef et al. |
| 2007/0055344 A1 | 3/2007 | Gittings et al. |
| 2007/0083258 A1 | 4/2007 | Falotico et al. |
| 2007/0098753 A1 | 5/2007 | Falotico et al. |
| 2007/0100432 A1 | 5/2007 | Case et al. |
| 2007/0141232 A1 | 6/2007 | Tochterman et al. |
| 2007/0156248 A1 | 7/2007 | Marco et al. |
| 2007/0173787 A1 | 7/2007 | Huang et al. |
| 2007/0173867 A1 | 7/2007 | Brenneman |
| 2007/0173868 A1 | 7/2007 | Bachinski et al. |
| 2007/0173878 A1 | 7/2007 | Heuser |
| 2007/0178129 A1 | 8/2007 | Flanagan |
| 2007/0179426 A1 | 8/2007 | Selden |
| 2007/0191872 A1 | 8/2007 | Stiger |
| 2007/0191943 A1 | 8/2007 | Shrivastava et al. |
| 2007/0203565 A1 | 8/2007 | Rust et al. |
| 2007/0213750 A1 | 9/2007 | Weadock |
| 2007/0231365 A1 | 10/2007 | Wang et al. |
| 2007/0244569 A1 | 10/2007 | Weber et al. |
| 2007/0249985 A1 | 10/2007 | Brenneman et al. |
| 2007/0255210 A1 | 11/2007 | Wahr et al. |
| 2007/0282157 A1 | 12/2007 | Rottenberg et al. |
| 2007/0299384 A1 | 12/2007 | Faul et al. |
| 2007/0299543 A1 | 12/2007 | Cartledge et al. |
| 2008/0009781 A1 | 1/2008 | Anwar et al. |
| 2008/0009939 A1 | 1/2008 | Gueriguian et al. |
| 2008/0015686 A1 | 1/2008 | Gale et al. |
| 2008/0021485 A1 | 1/2008 | Catanese et al. |
| 2008/0026034 A1 | 1/2008 | Cook et al. |
| 2008/0051883 A1 | 2/2008 | Llanos et al. |
| 2008/0051884 A1 | 2/2008 | Llanos et al. |
| 2008/0051885 A1 | 2/2008 | Llanos et al. |
| 2008/0063685 A1 | 3/2008 | Wang et al. |
| 2008/0071350 A1 | 3/2008 | Stinson |
| 2008/0071352 A1 | 3/2008 | Weber et al. |
| 2008/0082162 A1 | 4/2008 | Boismier et al. |
| 2008/0086107 A1 | 4/2008 | Roschak |
| 2008/0091264 A1 | 4/2008 | Machold et al. |
| 2008/0109069 A1 | 5/2008 | Coleman et al. |
| 2008/0119879 A1 | 5/2008 | Brenneman et al. |
| 2008/0161904 A1 | 7/2008 | Heuser et al. |
| 2008/0167595 A1 | 7/2008 | Porter et al. |
| 2008/0171944 A1 | 7/2008 | Brenneman et al. |
| 2008/0234842 A1 | 9/2008 | Zhang |
| 2009/0105654 A1 | 4/2009 | Kurth et al. |
| 2009/0125097 A1 | 5/2009 | Bruszewski et al. |
| 2009/0143713 A1 | 6/2009 | Van Dam et al. |
| 2009/0149947 A1 | 6/2009 | Frohwitter |
| 2009/0163847 A1 | 6/2009 | Kapadia |
| 2009/0187116 A1 | 7/2009 | Noishiki et al. |
| 2009/0216253 A1 | 8/2009 | Bell et al. |
| 2009/0221961 A1 | 9/2009 | Tal et al. |
| 2009/0234293 A1 | 9/2009 | Albrecht et al. |

(56) References Cited

U.S. PATENT DOCUMENTS

| | | |
|---|---|---|
| 2009/0275876 A1 | 11/2009 | Brenneman et al. |
| 2009/0281379 A1 | 11/2009 | Binmoeller et al. |
| 2010/0030321 A1 | 2/2010 | Mach |
| 2010/0106171 A1 | 4/2010 | Arepally et al. |
| 2010/0116279 A9 | 5/2010 | Cooper |
| 2010/0198041 A1 | 8/2010 | Christian et al. |
| 2010/0217382 A1 | 8/2010 | Chau et al. |
| 2010/0268313 A1 | 10/2010 | Conn |
| 2010/0268316 A1 | 10/2010 | Brenneman et al. |
| 2010/0298930 A1 | 11/2010 | Orlov |
| 2011/0092877 A1 | 4/2011 | Brenneman |
| 2011/0096036 A1 | 4/2011 | McIntosh et al. |
| 2011/0106118 A1 | 5/2011 | Son et al. |
| 2011/0112622 A1 | 5/2011 | Phan et al. |
| 2011/0130702 A1 | 6/2011 | Stergiopulos |
| 2011/0184504 A1 | 7/2011 | Ward et al. |
| 2011/0196190 A1 | 8/2011 | Farnan et al. |
| 2011/0213459 A1 | 9/2011 | Garrison et al. |
| 2011/0218477 A1 | 9/2011 | Keren et al. |
| 2011/0251482 A1 | 10/2011 | Kellerman et al. |
| 2011/0257723 A1 | 10/2011 | McNamara |
| 2011/0270149 A1 | 11/2011 | Faul et al. |
| 2012/0041371 A1 | 2/2012 | Tal et al. |
| 2012/0041544 A1 | 2/2012 | Wolf |
| 2012/0053686 A1 | 3/2012 | McNamara et al. |
| 2012/0089116 A9 | 4/2012 | Roschak |
| 2012/0101423 A1 | 4/2012 | Brenneman |
| 2012/0136426 A1 | 5/2012 | Phan et al. |
| 2012/0143141 A1 | 6/2012 | Verkaik et al. |
| 2012/0265229 A1 | 10/2012 | Rottenberg et al. |
| 2012/0265296 A1 | 10/2012 | McNamara et al. |
| 2012/0290077 A1 | 11/2012 | Aklog et al. |
| 2012/0316487 A1 | 12/2012 | Brenneman et al. |
| 2013/0006282 A1 | 1/2013 | Wilkinson |
| 2013/0022214 A1 | 1/2013 | Dickins et al. |
| 2013/0030521 A1 | 1/2013 | Nitzan et al. |
| 2013/0060186 A1 | 3/2013 | Brenneman et al. |
| 2013/0123827 A1 | 5/2013 | Kellerman et al. |
| 2013/0131773 A9 | 5/2013 | Brenneman et al. |
| 2013/0178784 A1 | 7/2013 | McNamara et al. |
| 2013/0184633 A1 | 7/2013 | McNamara et al. |
| 2013/0204175 A1 | 8/2013 | Sugimoto |
| 2013/0253342 A1 | 9/2013 | Griswold et al. |
| 2013/0261531 A1 | 10/2013 | Gallagher et al. |
| 2013/0281978 A1 | 10/2013 | Nance et al. |
| 2013/0281988 A1 | 10/2013 | Magnin et al. |
| 2014/0012368 A1 | 1/2014 | Sugimoto et al. |
| 2014/0031842 A1 | 1/2014 | Brenneman et al. |
| 2014/0121685 A1 | 5/2014 | Brenneman et al. |
| 2014/0183828 A1 | 7/2014 | Xu et al. |
| 2014/0194971 A1 | 7/2014 | McNamara |
| 2014/0203939 A1 | 7/2014 | Harrington et al. |
| 2014/0222040 A1 | 8/2014 | Park et al. |
| 2014/0276395 A1 | 9/2014 | Wilson et al. |
| 2014/0277054 A1 | 9/2014 | McNamara et al. |
| 2014/0278442 A1 | 9/2014 | Hong et al. |
| 2014/0350523 A1 | 11/2014 | Dehdashtian et al. |
| 2015/0039084 A1 | 2/2015 | Levi et al. |
| 2015/0119796 A1 | 4/2015 | Finch |
| 2015/0127030 A1 | 5/2015 | Brenneman |
| 2015/0141899 A1 | 5/2015 | Brenneman et al. |
| 2015/0148731 A1 | 5/2015 | Mcnamara et al. |
| 2015/0148826 A1 | 5/2015 | Dakin et al. |
| 2015/0151101 A1 | 6/2015 | Bonnette et al. |
| 2015/0196705 A1 | 7/2015 | Brenneman et al. |
| 2015/0217039 A1 | 8/2015 | Brenneman et al. |
| 2015/0238729 A1 | 8/2015 | Jenson et al. |
| 2015/0245908 A1 | 9/2015 | Nitzan et al. |
| 2015/0320330 A1 | 11/2015 | Sparks et al. |
| 2016/0022293 A1 | 1/2016 | Dubrul et al. |
| 2016/0022970 A1 | 1/2016 | Forcucci et al. |
| 2016/0058452 A1 | 3/2016 | Brenneman et al. |
| 2016/0120550 A1 | 5/2016 | McNamara et al. |
| 2016/0166381 A1 | 6/2016 | Sugimoto et al. |
| 2016/0220357 A1 | 8/2016 | Anand et al. |
| 2016/0270810 A1 | 9/2016 | Vardi et al. |
| 2016/0296317 A1 | 10/2016 | Timmermans et al. |
| 2016/0323977 A1 | 11/2016 | Sun et al. |
| 2017/0020540 A1 | 1/2017 | Chou et al. |
| 2017/0056633 A1 | 3/2017 | Aman et al. |
| 2017/0071603 A1 | 3/2017 | Brenneman |
| 2017/0071722 A1 | 3/2017 | Rafiee et al. |
| 2017/0090865 A1 | 3/2017 | Armstrong-Muntner et al. |
| 2017/0105839 A1 | 4/2017 | Subramanian et al. |
| 2017/0106176 A1 | 4/2017 | Taft et al. |
| 2017/0113026 A1 | 4/2017 | Finch |
| 2017/0128705 A1 | 5/2017 | Forcucci et al. |
| 2017/0232241 A1 | 8/2017 | Brenneman et al. |
| 2017/0281339 A1 | 10/2017 | Levi et al. |
| 2017/0303959 A1 | 10/2017 | Feng et al. |
| 2017/0319823 A1 | 11/2017 | Yacoby et al. |
| 2017/0340460 A1 | 11/2017 | Rosen et al. |
| 2018/0049742 A1 | 2/2018 | Brenneman et al. |
| 2018/0116791 A9 | 5/2018 | Nitzan et al. |
| 2018/0177516 A1 | 6/2018 | Vardi et al. |
| 2018/0185153 A1 | 7/2018 | Bishop et al. |
| 2018/0206845 A1 | 7/2018 | Brenneman et al. |
| 2018/0207412 A1 | 7/2018 | Malek et al. |
| 2018/0243071 A1 | 8/2018 | Eigler et al. |
| 2018/0256865 A1 | 9/2018 | Finch et al. |
| 2018/0280667 A1 | 10/2018 | Keren |
| 2019/0008628 A1 | 1/2019 | Eigler et al. |
| 2019/0083076 A1 | 3/2019 | Alanbaei |
| 2019/0110911 A1 | 4/2019 | Nae et al. |
| 2019/0142571 A1 | 5/2019 | Chu et al. |
| 2019/0240391 A1 | 8/2019 | Brenneman et al. |
| 2019/0254814 A1 | 8/2019 | Nitzan et al. |
| 2019/0262118 A1 | 8/2019 | Eigler et al. |
| 2019/0269392 A1 | 9/2019 | Celermajer et al. |
| 2019/0298909 A1 | 10/2019 | Cully et al. |
| 2019/0351210 A1 | 11/2019 | Solomon et al. |
| 2020/0054867 A1 | 2/2020 | Schwartz et al. |
| 2020/0085600 A1 | 3/2020 | Schwartz et al. |
| 2020/0101270 A1 | 4/2020 | Sutherland |
| 2020/0170662 A1 | 6/2020 | Vardi et al. |
| 2020/0187945 A1 | 6/2020 | Rowe et al. |
| 2020/0254228 A1 | 8/2020 | Taft et al. |
| 2020/0261704 A1 | 8/2020 | Wang et al. |
| 2020/0289196 A1 | 9/2020 | Arevalos et al. |
| 2020/0315599 A1 | 10/2020 | Nae et al. |
| 2020/0368505 A1 | 11/2020 | Nae et al. |
| 2020/0391016 A1 | 12/2020 | Passman et al. |
| 2021/0007790 A1 | 1/2021 | Takahashi et al. |
| 2021/0007791 A1 | 1/2021 | Takahashi et al. |
| 2021/0007800 A1 | 1/2021 | Takahashi et al. |
| 2021/0045691 A1 | 2/2021 | Zou et al. |
| 2021/0059650 A1 | 3/2021 | Eidenschink et al. |
| 2021/0077186 A1 | 3/2021 | Pate et al. |
| 2021/0085935 A1 | 3/2021 | Fahey et al. |
| 2021/0092522 A1 | 3/2021 | Draper et al. |
| 2021/0121179 A1 | 4/2021 | Ben-David et al. |
| 2021/0153776 A1 | 5/2021 | Minar et al. |
| 2021/0161637 A1 | 6/2021 | Eigler et al. |
| 2021/0177508 A1 | 6/2021 | Kellerman |
| 2021/0236138 A1 | 8/2021 | Perszyk et al. |
| 2021/0290214 A1 | 9/2021 | Cole et al. |
| 2021/0338240 A1 | 11/2021 | Rowe et al. |
| 2021/0369321 A1 | 12/2021 | Yang et al. |
| 2021/0401494 A1 | 12/2021 | Passman et al. |
| 2022/0001154 A1 | 1/2022 | Rowe et al. |
| 2022/0008014 A1 | 1/2022 | Rowe et al. |
| 2022/0031327 A1 | 2/2022 | Manash et al. |
| 2022/0039667 A1 | 2/2022 | Schmitt et al. |
| 2022/0039671 A1 | 2/2022 | Fahey |
| 2022/0039833 A1 | 2/2022 | Thai et al. |
| 2022/0088355 A1 | 3/2022 | Rabito et al. |
| 2022/0096087 A1 | 3/2022 | Valdez |
| 2022/0110679 A1 | 4/2022 | Wang et al. |
| 2022/0142652 A1 | 5/2022 | Alexander et al. |
| 2022/0151618 A1 | 5/2022 | Eigler et al. |
| 2022/0151784 A1 | 5/2022 | Eigler et al. |
| 2022/0168015 A1 | 6/2022 | Murray et al. |
| 2022/0184356 A1 | 6/2022 | Nae et al. |
| 2022/0202443 A1 | 6/2022 | Thai et al. |

(56) References Cited

U.S. PATENT DOCUMENTS

| | | |
|---|---|---|
| 2022/0203078 A1 | 6/2022 | May |
| 2022/0211380 A1 | 7/2022 | Pate |
| 2022/0218352 A1 | 7/2022 | O'Halloran et al. |
| 2022/0218964 A1 | 7/2022 | Fahey et al. |
| 2022/0226000 A1 | 7/2022 | Alexander et al. |
| 2022/0226623 A1 | 7/2022 | Fahey et al. |
| 2022/0241564 A1 | 8/2022 | Shang et al. |
| 2022/0241565 A1 | 8/2022 | Nae et al. |
| 2022/0257904 A1 | 8/2022 | Passman et al. |
| 2022/0273279 A1 | 9/2022 | Valdez et al. |
| 2022/0280160 A1 | 9/2022 | Sharma |
| 2022/0280760 A1 | 9/2022 | Thai et al. |
| 2022/0296865 A1 | 9/2022 | Rafiee et al. |
| 2022/0313234 A1 | 10/2022 | Mcnamara et al. |
| 2022/0323012 A1 | 10/2022 | Pool et al. |
| 2022/0323196 A1 | 10/2022 | Rafiee et al. |
| 2022/0346936 A1 | 11/2022 | Scutti et al. |
| 2022/0347446 A1 | 11/2022 | Fahey et al. |
| 2022/0370120 A1 | 11/2022 | Yang et al. |
| 2022/0379100 A1* | 12/2022 | Gutierrez ............ A61M 27/002 |
| 2022/0387009 A1 | 12/2022 | Bukhdruker et al. |
| 2023/0022499 A1 | 1/2023 | Rowe et al. |
| 2023/0099410 A1 | 3/2023 | Primeaux |
| 2023/0165672 A1 | 6/2023 | Fahey et al. |
| 2023/0181214 A1 | 6/2023 | Vardi et al. |
| 2023/0191093 A1 | 6/2023 | Nae et al. |
| 2023/0263949 A1 | 8/2023 | Passman et al. |
| 2023/0285133 A1 | 9/2023 | Eigler et al. |
| 2023/0330398 A1 | 10/2023 | Nae et al. |

FOREIGN PATENT DOCUMENTS

| | | | |
|---|---|---|---|
| WO | WO-2020123338 A1 | 6/2020 | |
| WO | 2020215090 A1 | 10/2020 | |
| WO | 2021091566 A1 | 5/2021 | |
| WO | 2022031317 A1 | 2/2022 | |
| WO | 2022060630 A1 | 3/2022 | |
| WO | 2022133070 A1 | 6/2022 | |
| WO | 2022169865 A1 | 8/2022 | |
| WO | 2022177737 A1 | 8/2022 | |
| WO | 2022197454 A1 | 9/2022 | |
| WO | 2022197455 A1 | 9/2022 | |
| WO | 2022232133 A1 | 11/2022 | |
| WO | 2022246158 A1 | 11/2022 | |
| WO | 2022246166 A1 | 11/2022 | |
| WO | 2022246168 A1 | 11/2022 | |
| WO | 2022271473 A1 | 12/2022 | |
| WO | 2023022883 A1 | 2/2023 | |
| WO | 2023027926 A1 | 3/2023 | |
| WO | 2023079498 A1 | 5/2023 | |
| WO | 2023081127 A1 | 5/2023 | |
| WO | 2023081129 A1 | 5/2023 | |
| WO | 2023154235 A1 | 8/2023 | |
| WO | 2023154308 A1 | 8/2023 | |
| WO | 2023172435 A1 | 9/2023 | |
| WO | 2023172436 A1 | 9/2023 | |
| WO | 2023196243 A1 | 10/2023 | |
| WO | 2023239784 A1 | 12/2023 | |
| WO | 2023239785 A1 | 12/2023 | |
| WO | 2023239788 A2 | 12/2023 | |

OTHER PUBLICATIONS

Kong, et al.—Creation of an Intra-atrial Communication With a New Amplatzer Shunt Prosthesis, Catheterization and Cardiovascular Interventions 56:267-271 (2002).

P.K. Kong, et al., Title: Unroofed Coronary Sinus and Persistent Left Superior Vena Cava, The European Society of Cardiology, 2006, p. 398401.

Ruebben et al., "Arteriovenous fistulas induced by femoral arterial catheterization: percutaneous treatment," Radiology, 209:729, 1998.

Vandhana Scheller, et al., Title: Coronary Sinus to Left Atrial Communication, Case Report in Medicine, Ohio Heart and Vascular Center, vol. 2009, Article ID 790715, pp. 13.

\* cited by examiner

400

DELIVER IMPLANT
TO CORONARY
SINUS VIA RIGHT
ATRIUM
402

PASS IMPLANT
THROUGH
OPENING IN
CORONARY SINUS
WALL
404

ANCHOR IMPLANT
TO OPENING IN
CORONARY SINUS
WALL    *406*

504a   502   2   500c 504b   508a 19   508b

*700*

DELIVER IMPLANT TO CORONARY SINUS VIA RIGHT ATRIUM *702*

PASS IMPLANT THROUGH OPENING IN CORONARY SINUS WALL *704*

ANCHOR IMPLANT
TO OPENING IN
CORONARY SINUS
WALL   *706*

*1100*

DELIVER IMPLANT
TO CORONARY
SINUS VIA RIGHT
ATRIUM   *1102*

RETRACT SHEATH
TO EXPOSE UPPER
SHUNT AND
LOWER SHUNT   *1104*

EXTEND UPPER
SHUNT THROUGH
TISSUE WALL
OPENING   *1106*

FLEXIBLE SHUNT IMPLANTS

RELATED APPLICATION

This application is a continuation of International Patent Application No. PCT/US2021/063773, filed Dec. 16, 2021, which claims the benefit of U.S. Patent Application No. 63/199,323, filed Dec. 18, 2020, the entire disclosures of each of which are incorporated by reference for all purposes.

BACKGROUND

Field

The present invention relates generally to the field of medical devices and procedures.

Description of Related Art

In percutaneous delivery systems for delivering certain medical implant devices to target locations at least in part through a patient's vasculature, certain anatomical and device dimensions can limit the size, shape, and/or configuration of medical implant devices delivered using such systems.

SUMMARY

For purposes of summarizing the disclosure, certain aspects, advantages and novel features have been described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

Some implementations of the present disclosure relate to a delivery system comprising a catheter configured to be delivered through a blood flow pathway of a heart and an implant configured to maintain an opening in a tissue wall to allow blood flow through the opening and into the blood flow pathway and be delivered via the catheter. The implant is at least partially composed of a flexible material to allow the implant to bend with the catheter.

The implant may be configured to be crimped around an outer surface of the catheter. In some embodiments, the implant is at least partially composed of braided cords. The implant may be at least partially composed of a coiled cord.

In some embodiments, the implant comprises a puncture element configured to puncture through a tissue wall to create the opening in the tissue wall. The puncture element may be further configured to anchor the implant to the tissue wall. In some embodiments, the implant further comprises an anchoring element and the puncture element and the anchoring element are configured to anchor to opposing sides of the tissue wall.

The implant may comprise a first tubular portion and a second tubular portion. In some embodiments, the first tubular portion is configured to bend away from the second tubular portion to allow the first tubular portion to enter the opening in the tissue wall. The second tubular portion may be configured to extend along the blood flow pathway and beyond the opening in the tissue wall.

In some embodiments, the first tubular portion and the second tubular portion are separate devices. The first tubular portion and the second tubular portion may extend from a common base portion. In some embodiments, the first tubular portion is at least partially composed of a shape-memory material.

The delivery system may further comprise a sheath configured to at least partially enclose the implant and retract to at least partially expose the implant and allow the implant to expand. In some embodiments, the blood flow pathway is a coronary sinus and the opening creates a flow pathway between a left atrium and the coronary sinus.

Some implementations of the present disclosure relate to a method comprising delivering an implant enclosed at least partially by a sheath to a coronary sinus via a right atrium. The implant is at least partially composed of braided or coiled cords to allow the implant to bend into the coronary sinus. The method further comprises puncturing a tissue wall of the coronary sinus to create an opening between a left atrium and the coronary sinus, retracting the sheath to expose the implant, and anchoring the implant at the opening. The implant is configured to maintain the opening.

The implant may comprise a puncture element. Puncturing the tissue wall may be performed using the puncture element.

In some embodiments, anchoring the implant at the opening involves contacting the tissue wall with the puncture element. The puncture element may be configured to establish a single point of contact with the tissue wall.

The implant may comprise a first tubular portion and a second tubular portion. Retracting the sheath may allow the first tubular portion to bend away from the second tubular portion.

In accordance with some implementations of the present disclosure, a medical implant comprises means for maintaining an opening through a tissue wall of a heart. The opening creates a blood flow path from a first chamber of a heart to a blood flow pathway of the heart. The means for maintaining the opening is/are configured to bend to facilitate delivery into the blood flow pathway and the first chamber. The medical implant further comprises means for anchoring to the tissue wall at the opening.

The medical implant may further comprise means for puncturing the tissue wall to create the opening.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements. However, it should be understood that the use of similar reference numbers in connection with multiple drawings does not necessarily imply similarity between respective embodiments associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some embodiments or configurations.

DETAILED DESCRIPTION

Figure 1:
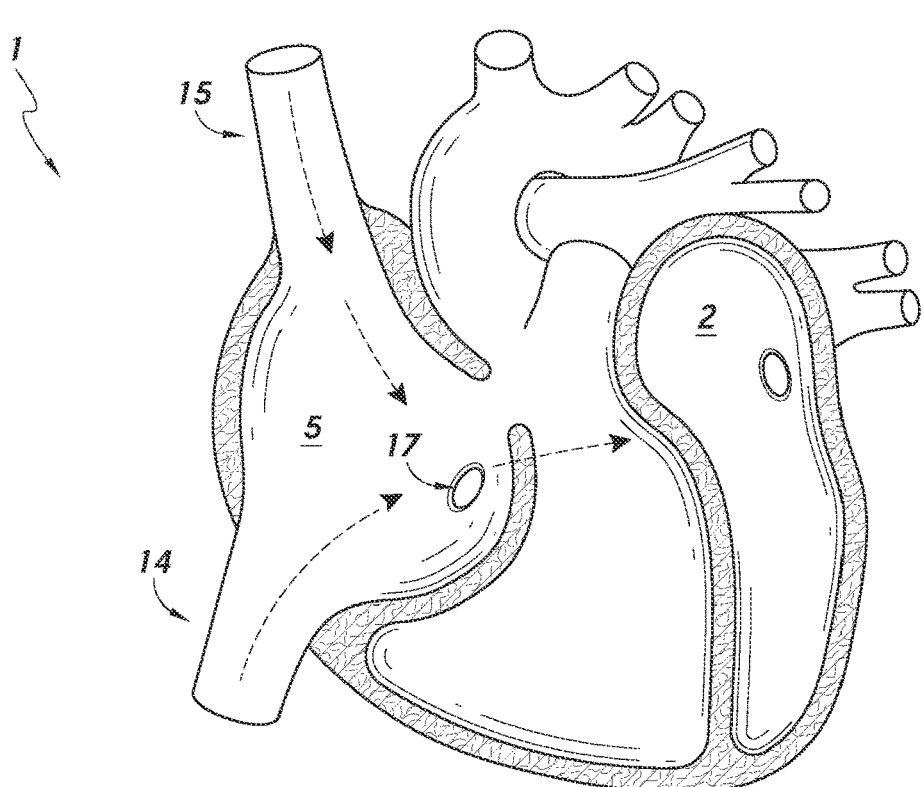
FIG. 1 illustrates several access pathways for maneuvering guidewires and/or catheters in and around the heart to deploy compressible implants in accordance with some embodiments.

The headings provided herein are for convenience only and do not necessarily affect the scope or meaning of the claimed invention.

Overview

Heart failure is a common and potentially lethal condition affecting humans, with sub-optimal clinical outcomes often resulting in symptoms, morbidity and/or mortality, despite maximal medical treatment. In particular, "diastolic heart failure" refers to the clinical syndrome of heart failure occurring in the context of preserved left ventricular systolic function (ejection fraction) and in the absence of major valvular disease. This condition is characterized by a stiff left ventricle with decreased compliance and impaired relaxation, which leads to increased end-diastolic pressure. Approximately one third of patients with heart failure have diastolic heart failure and there are very few, if any, proven effective treatments.

Symptoms of diastolic heart failure are due, at least in a large part, to an elevation in pressure in the left atrium. Elevated Left Atrial Pressure (LAP) is present in several abnormal heart conditions, including Heart Failure (HF). In addition to diastolic heart failure, a number of other medical conditions, including systolic dysfunction of the left ventricle and valve disease, can lead to elevated pressures in the left atrium. Both Heart Failure with Preserved Ejection Fraction (HFpEF) and Heart Failure with Reduced Ejection Fraction (HFrEF) can exhibit elevated LAP. It has been hypothesized that both subgroups of HF might benefit from a reduction in LAP, which in turn reduces the systolic preload on the left ventricle, Left Ventricular End Diastolic Pressure (LVEDP). It could also relieve pressure on the pulmonary circulation, reducing the risk of pulmonary edema, improving respiration and improving patient comfort.

Pulmonary hypertension (PH) is defined as a rise in mean pressure in the main pulmonary artery. PH may arise from many different causes, but, in all patients, has been shown to increase mortality rate. A deadly form of PH arises in the very small branches of the pulmonary arteries and is known as Pulmonary Arterial Hypertension (PAH). In PAH, the cells inside the small arteries multiply due to injury or disease, decreasing the area inside of the artery and thickening the arterial wall. As a result, these small pulmonary arteries narrow and stiffen, causing blood flow to become restricted and upstream pressures to rise. This increase in pressure in the main pulmonary artery is the common connection between all forms of PH regardless of underlying cause. Despite previous attempts, there is a need for an improved way to reduce elevated pressure in the left atrium, as well as other susceptible heart chambers such as the pulmonary artery.

The present disclosure provides methods and devices (including various implants) for shunting blood within a human body. The term "implant" is used herein according to its plain and ordinary meaning and may refer to any medical implant, frame, valve, shunt, stent, anchor, and/or similar devices for use in treating various conditions in a human body. Implants may be delivered via catheter (i.e., transcatheter) for various medical procedures and may have a generally sturdy and/or flexible structure. The term "catheter" is used herein according to its broad and ordinary meaning and may include any tube, sheath, steerable sheath, steerable catheters, and/or any other type of elongate tubular delivery device comprising an inner lumen configured to slidably receive instrumentation, such as for positioning within an atrium or coronary sinus, including for example delivery catheters and/or cannulas. In some cases, an implant may be composed of a shape-memory alloy (e.g., Nitinol) and/or may have a pre-defined shape and/or structure. The implant may be configured to be shaped and/or compressed to fit into and/or around a catheter. In some cases, an implant may have an elliptical and/or cylindrical form and/or may comprise an interweaving pattern of materials.

Some embodiments described herein provide methods and/or systems for shunting blood within a body of a patient. While some embodiments may be directed to delivery of shunt systems into the coronary sinus ostium (CSO) from the superior vena cava, the methods and/or systems described herein may be applicable to other areas of the body. For example, some methods and/or devices described herein may advantageously be configured for delivery of shunt devices into various challenging cardiovascular anatomies.

Some known and/or conventional shunt devices can include pre-shaped stents and/or similar devices. Such devices can have a generally stiff and/or less-maneuverable structure, particularly when collapsed down during a delivery process. Some embodiments herein advantageously provide flexible and/or maneuverable shunt devices that can facilitate delivery through various pathways in a patient's body.

The following includes a general description of human cardiac anatomy that is relevant to certain inventive features and embodiments disclosed herein and is included to provide context for certain aspects of the present disclosure. In humans and other vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice. The four valves ensure that blood does not flow in the wrong direction during the cardiac cycle; that is, to ensure that the blood does not back flow through the valve. Blood flows from the venous system and right atrium through the tricuspid valve to the right ventricle, then from the right ventricle through the pulmonary valve to the pulmonary artery and the lungs. Oxygenated blood then flows through the mitral valve from the left atrium to the left ventricle, and finally from the left ventricle through the aortic valve to the aorta/arterial system.

FIG. 1 illustrates several access pathways for maneuvering guidewires and catheters in and around the heart 1 to deploy compressible medical implants (e.g., frames) of the present application. For instance, access may be from above via either the subclavian vein or jugular vein into the superior vena cava (SVC) 15, right atrium (RA) 5 and from there into the coronary sinus ostium (CSO) 17. Alternatively, the access path may start in the femoral vein and through the inferior vena cava (IVC) 14 into the heart 1. Other access routes may also be used, and each typically utilizes a percutaneous incision through which the guidewire and catheter are inserted into the vasculature, normally through a sealed introducer, and from there the physician controls the distal ends of the devices from outside the body.

Figure 2:
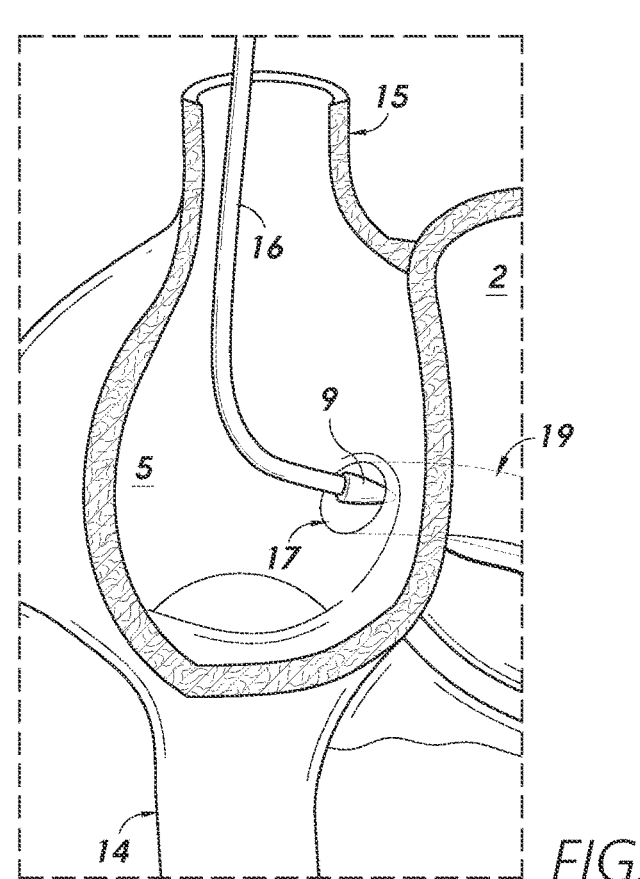
FIG. 2 depicts a procedure for deploying implants in accordance with some embodiments.

FIG. 2 depicts an example method for deploying medical implants, wherein a guidewire and/or catheter 16 is/are introduced through the subclavian or jugular vein, through the SVC 15 and into the coronary sinus 19. In some instances, a guidewire may be used to provide a path, after which an introducer sheath (not shown) may be routed along the guidewire and into the patient's vasculature, typically with the use of a dilator 9 and/or atraumatic tip. FIG. 2 shows a deployment catheter 16 extending from the SVC 15 to the CSO 17 and into the coronary sinus 19 of the heart 1. The deployment catheter 16 can be passed through an introducer sheath which can provide a hemostatic valve to prevent blood loss.

The deployment catheter 16 may be about 30 cm long, and the guidewire may be somewhat longer for ease of use. In some embodiments, the deployment catheter may function to form and/or prepare an opening in the wall of the left atrium 2, and a separate placement or delivery catheter may be used for delivery of an expandable implant. In other embodiments, the deployment catheter may be used as both the puncture preparation and implant placement catheter with full functionality. In the present application, the terms "deployment catheter" or "delivery catheter" will be used to represent a catheter or introducer with one or both of these functions.

Since the coronary sinus 19 is largely contiguous around the left atrium 2, there are a variety of possible acceptable placements for implants. The site selected for placement of an implant (e.g., a shunt) may be made in an area where the tissue of the particular patient is less thick or less dense, as determined beforehand by non-invasive diagnostic means, such as a CT scan or radiographic technique, such as fluoroscopy or intravascular coronary echo (IVUS).

Some methods to reduce LAP involve utilizing an implant between the left atrium 2 and the right atrium 5, through the interatrial septum therebetween. This is a convenient approach, as the two structures are adjacent and transseptal access is common practice. However, there may be a possibility of emboli travelling from the right side of the heart to the left, which presents a stroke risk. This event should only happen if the right atrium pressures go above left atrium pressures; primarily during discrete events like coughing, sneezing, Valsalva maneuver, or bowel movements. The anatomical position of the septum would naturally allow emboli to travel freely between the atria if an implant was present and the pressure gradient flipped. This can be mitigated by a valve or filter element in the implant, but there may still be risk that emboli will cross over.

Implanting to the coronary sinus 19 offers some distinct advantages, including that the coronary sinus 19 is much less likely to have emboli present for several reasons. First, the blood draining from the coronary vasculature into the right atrium 5 has just passed through capillaries, so it is essentially filtered blood. Second, the CSO 17 of the coronary sinus 19 in the right atrium 5 is often partially covered by a pseudo-valve called the Thebesian Valve. The Thebesian Valve is not always present, but some studies show it is present in >60% of hearts and it would act as a natural "guard dog" to the coronary sinus to prevent emboli from entering in the event of a spike in right atrium pressure. Third, pressure gradient between the coronary sinus 19 and the right atrium 5 into which it drains is very low, meaning that emboli in the right atrium 5 is likely to remain there. Fourth, in the event that emboli do enter the coronary sinus 19, there will be a much greater gradient between the right atrium 5 and the coronary vasculature than between the right atrium 5 and the left atrium 2. Most likely emboli would travel further down the coronary vasculature until right atrium pressure returned to normal and then the emboli would return directly to the right atrium 5.

Some additional advantages to locating implants between the left atrium 2 and the coronary sinus 19 can include that this anatomy is less mobile and/or more stable than the septum and/or may preserve the septum for later transseptal access for alternate therapies, and it could potentially have other therapeutic benefits. By diverting left atrial blood into the coronary sinus 19, sinus pressures may increase by a small amount. This would cause blood in the coronary vasculature to travel more slowly through the heart, increasing perfusion and oxygen transfer, which would be more efficient and also could help a dying heart muscle to recover. The preservation of transseptal access also is a very significant advantage because HF patients often have a number of other comorbidities like Atrial Fibrillation (AF) and Mitral Regurgitation (MR) and several of the therapies for treating these conditions require a transseptal approach.

An implant may also be positioned within chambers and/or vessels and/or between other cardiac chambers, such as between the pulmonary artery and right atrium 5. Implants may be desirably implanted within the wall of the pulmonary artery using the deployment tools described herein, with the catheters approaching from above and passing through the pulmonary artery. As explained above, pulmonary hypertension (PH) is defined as a rise in mean pressure in the main pulmonary artery. Blood flows through shunt implants from the pulmonary artery into the right atrium 5 if the pressure differential causes flow in that direction, which attenuates pressure and reduces damage to the pulmonary artery. The purpose is to attenuate pressure spikes in the pulmonary artery. Implants may also extend from the pulmonary artery to other heart chambers (e.g., left atrium 2) and/or blood vessels. In some embodiments, implants may further contain a one-way valve for preventing backflow, or a check valve for allowing blood to pass only above a designated pressure.

Tracking shunt delivery systems (e.g., on a guidewire) into the coronary sinus ostium (CSO) 17 from the superior vena cava 15 can often be challenging due at least in part to the CSO-level insertion (CSLI) distance, which may measure a distance between the bottom of the CSO 17 and the bottom of the right atrium 5. If an implant is at least partially stiff and/or creates a stiff section within a portion of the catheter 16, it can make it difficult for surgeons to track the catheter 16 through the CSO 17 and/or other anatomies. In some cases, the catheter 16 can catch on the ridge below the CSO 17 and/or the catheter must form a large "bow" shape into the right atrium 5 (as shown in FIG. 2) when tracking the catheter 16 over a guidewire. In some cases, bowing of the catheter 16 as shown in FIG. 2 can result in a loss of guidewire access due to for example, a guidewire extending from the catheter 16 beyond an access point within the coronary sinus 19.

Some implants described herein may be at least partially compressible and/or expandable. Implants described herein may have various features to simplify and/or improve delivery procedures for surgeons. For example, an implant may be at least partially flexible, compressible, and/or elastic to allow the implant to be shaped and/or molded as necessary/desired to fit into/onto delivery catheters having various sizes and/or shapes.

Moreover, an implant may be configured to fit into various openings created in tissue walls having various sizes and/or shapes. A tissue wall may be situated between a first anatomical chamber (e.g., the coronary sinus 19) and a second anatomical chamber (e.g., the left atrium 2). In some embodiments, an opening may be created through the tissue wall and/or an implant may be configured to fit at least partially within the opening. The opening may represent a blood flow path between the first anatomical chamber and the second anatomical chamber. In some embodiments, an implant may be configured to maintain the opening and/or the blood flow path from the first anatomical chamber to the second anatomical chamber.

Expandable Shunt Implants

Figures 3A, 3B:
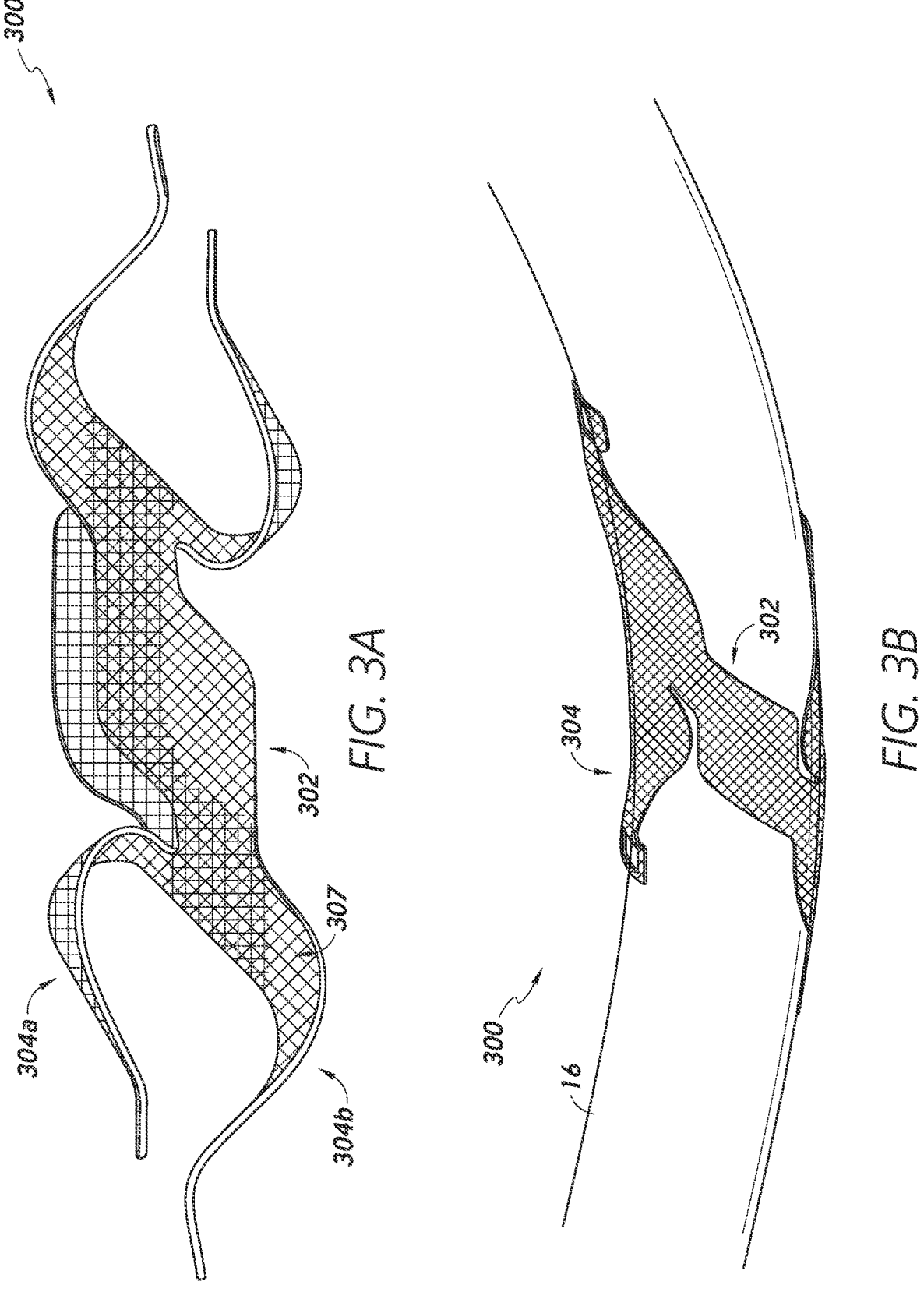
FIGS. 3A and 3B illustrate a flexible shunt implant in accordance with some embodiments.

FIGS. 3A and 3B illustrate a flexible shunt implant 300 in accordance with some embodiments. The implant 300 may comprise any of a variety of features and/or components configured to treat various medical conditions. For example, the implant 300 may be configured to maintain an opening in a tissue wall and/or allow blood flow through the tissue wall. In some embodiments, the implant 300 may comprise a central flow portion 302 which may be configured to be situated at least partially within an opening in a tissue wall. The central flow portion 302 may be configured to create and/or maintain an opening between two anatomical chambers. In some embodiments, the implant 300 may comprise multiple separate components which may be attached, connected, and/or otherwise joined to form a single device. For example, the central flow portion 302 may comprise multiple components to form a generally tubular shape which may approximate a shape of an opening in a tissue wall.

The implant 300 may be at least partially composed of braided materials, which may include stainless steel, Nitinol, and/or other metals. At least a portion of the implant 300 may be configured to collapse to a smaller diameter for delivery while maintaining flexibility of the implant 300. In some embodiments, at least a portion of the implant 300 may be configured for delivery into the body on an outer surface and/or outer diameter of a catheter 16, as shown in FIG. 3B.

For example, the implant 300 may be configured to be crimped onto the outer surface of the catheter 16. The implant 300 may be crimped down to the catheter as tightly as possible to minimize an increase in diameter of the catheter 16 caused by the implant 300. In some embodiments, at least a portion of the implant 300 may be covered by a tubular sheath (not shown) configured to surround at least a portion of the implant 300. The sheath may be configured to prevent the implant 300 from expanding from a crimped configuration. In some embodiments, additional and/or alternative devices and/or methods may be used to prevent expansion of the implant 300. For example, one or more wires may be attached to the implant 300 to hold the implant 300 tightly against the catheter 16 during delivery into the body.

The implant 300 may be configured to have maximal flexibility during delivery into the body to prevent the implant 300 from hindering bendability of the catheter 16. In some embodiments, the implant 300 may be configured to maintain a level of flexibility while crimped onto the catheter 16. The flexible shunt implant 300 may comprise a central flow portion 302 composed of a network of braided and/or interlocking cords 307, which may include wires, sutures, strings, fibers, and/or various other elongate devices. One or more cords 307 may interact with each other in a weaving/interweaving and/or braiding pattern. For example, a first cord may pass over a second cord, under a third cord, over a fourth cord, and so on. Accordingly, the one or more cords 307 may have at least some flexibility such that a cord 307 may be configured to bend over and/or under other cords 307. For example, one or more cords 307 may be composed of Nitinol and/or another material that may be configured to at least partially bend and/or stretch.

The flow portion 302 may include any number of cords 307. In some embodiments, the flow portion 302 may comprise a single cord 307 configured to interweave with itself. By increasing the number of cords 307 and/or an amount of interweaving of the one or more cords 307, gaps between the cords 307 and/or different sections of a single cord 307 may be minimized to improve prevention and/or reduction of in-growth of tissue. Moreover, each of the cords 307 may have any thickness and may be designed to minimize gaps while maximizing expandability of the flow portion 302.

The flow portion 302 may be configured to be situated at least partially within an opening in a tissue wall. The tissue wall may have a first side and a second side, and the opening may represent a gap through the tissue wall. A "thickness" of the tissue wall may refer to a distance between the first side and a second side of the tissue wall.

The one or more cords 307 of the flow portion 302 may form a cylindrical or other shape to approximate a shape of an opening in a tissue wall. In some embodiments, the opening may be widened in all directions approximately evenly from a puncture point to form an approximately circular opening having a certain diameter. Accordingly, the flow portion 302 may have an at least partially rounded and/or circular form.

In some embodiments, the flexible shunt implant 300 may be in a compacted and/or otherwise flexible form at delivery. For example, at delivery, the one or more cords 307 may be situated relatively close together with minimal gaps between the one or more cords 307. As the tissue wall expands, the one or more cords 307 may gradually separate and/or stretch to create a greater length of the flexible shunt implant 300. In some embodiments, the one or more cords 307 may be configured to stretch in response to expansion of the tissue wall. For example, at delivery, the one or more cords 307 may be in a natural resting state and/or may be only minimally stretched. As the tissue wall expands, at least some of the one or more cords 307 may stretch and/or at least partially separate to create a greater length of the flexible shunt implant 300.

The flexible shunt implant 300 may comprise one or more anchoring arms 304, which may include any means for anchoring a shunt implant to a catheter 16 and/or area of tissue within a body. The one or more anchoring arms 304 (e.g., including a first anchoring arm 304a and/or a second anchoring arm 304b) may be configured to anchor to/into a tissue wall. While the flexible shunt implant 300 is shown having two pairs of anchoring arms 304, the flexible shunt implant 300 may have any number of anchoring arms 304. In some embodiments, the flexible shunt implant 300 may comprise one or more anchoring arms 304 at a first end of the flexible shunt implant 300 and/or one or more anchoring arms 304 at or near a second end of the flexible shunt implant 300. An anchoring arm 304 may attach to and/or extend from any portion of the implant 300, including at one or more cords 307.

In some embodiments, each of the cords 307 and/or anchoring arms 304 may be composed of a common material or different materials. In some embodiments, any of the cords 307 and/or anchoring arms 304 may be composed of Nitinol and/or other metal, plastic, polymer, and/or other material Various features of the shunt implant 300, including the central flow portion 302 and/or anchoring arms 304 described herein, may be applied to the shunt devices described and/or illustrated in other figures of the present application. For example, any description with respect to the shunt implant 300 illustrated in FIGS. 3A and 3B may be similarly applied to the shunt implant 601 in FIG. 6 and/or the shunt implant 901 in FIGS. 9A and/or 9B. Moreover, while other shunts shown and/or described with respect to other figures may not include cords 307 as shown in FIGS. 3A and 3B, it will be understood that the shunts described with respect to other figures may comprise cords 307. Similarly, the various features described with respect to other figures herein may be added to the shunt implant 300 of FIGS. 3A and 3B or other figures herein even if not depicted in or described with respect to each figure. While the shunt implant 300 is shown including both a central flow portion 302 and anchoring arms 304, the shunt implant 300 may in some embodiments not include anchoring arms 304.

In some embodiments, the implant 300 may be configured to be movable between an expanded configuration and a collapsed configuration to facilitate passage through a lumen of a catheter. For example, the central flow portion 302 may be configured to be crimped and/or otherwise compacted to fit around an exterior surface of the catheter 16. Crimping may involve a reduction in diameter of the central flow portion 302 and/or an increase in length of the implant 300. When the implant 300 is crimped, at least a portion of the implant 300 may create resistive force in response to crimping pressure.

The central flow portion 302 may be configured to expand to a pre-defined shape (e.g., the shape and/or size shown in FIG. 3A) and/or size during and/or after removal from a deliver device (e.g., a catheter 16). The implant 300 may further comprise one or more anchoring arms 304, which may include flanges, arms, anchors, and/or other devices. In some embodiments, the one or more anchoring arms 304 (e.g., the first anchoring arm 304a and/or second anchoring arm 304b) may be configured to extend generally perpendicularly (i.e., forming a "T" shape) from the central flow portion. For example, the first anchoring arm 304a and the second anchoring arm 304b may be configured to lay flatly along a common plane. The one or more anchoring arms 304 may have a generally flat, curved, and/or wavy form. In some embodiments, the one or more anchoring arms 304 may be configured to at least partially collapse and/or compress to facilitate passage through the lumen of the catheter and/or may be configured to expand during and/or after delivery within the body to contact and/or attach to a tissue wall. Expansion of the implant 300 may be initiated, for example, by retraction of an outer sheath of the catheter relative to an inner support sheath. The implant 300 may be collapsed (e.g., crimped) into a generally tubular configuration. In some embodiments, the anchoring arms 304 may be configured to spring open when the restraining outer sheath retracts. The anchoring arms 304 may expand generally in opposite directions in a common plane to form a T-shape (see FIG. 3B), as opposed to expanding in a circular fashion. Radiopaque markers on the anchoring arms 304 and/or central flow portion 302 may be provided to facilitate positioning immediately within the body.

A pair of anchoring arms 304 (e.g., a first anchoring arm 304a and a second anchoring arm 304b) may be configured to form a clamping (i.e., pinching) pair of anchoring arms 304. The pairs of anchoring arms 304 may be configured to apply a compressive force to a tissue wall to hold the implant 300 in place. The amount of compressive force may be relatively small to avoid damage to the tissue wall while sufficient to hold the implant 300 in place. For example, gaps separating the pairs of anchoring arms may be calibrated to avoid excessive clamping and/or necrosis of the tissue. The anchoring arms 304 may be configured to secure the implant 300 on generally opposite sides of the tissue wall and/or on generally opposite sides of an opening in the tissue wall. The central flow portion 302 may be configured to be aligned generally perpendicularly to the tissue wall so as to maintain an open flow path between the chambers on either side of the tissue wall.

Components of the implant 300 may be configured to naturally self-expand due to inherent springiness and/or flexibility of the components. For example, various components (e.g., the central flow portion 302 and/or anchoring arms 304) may be at least partially composed of an elastic material such as Nitinol. In some embodiments, the central flow portion 302 may be fabricated by laser cutting a Nitinol tube.

Figures 1, 2, 4, 5:
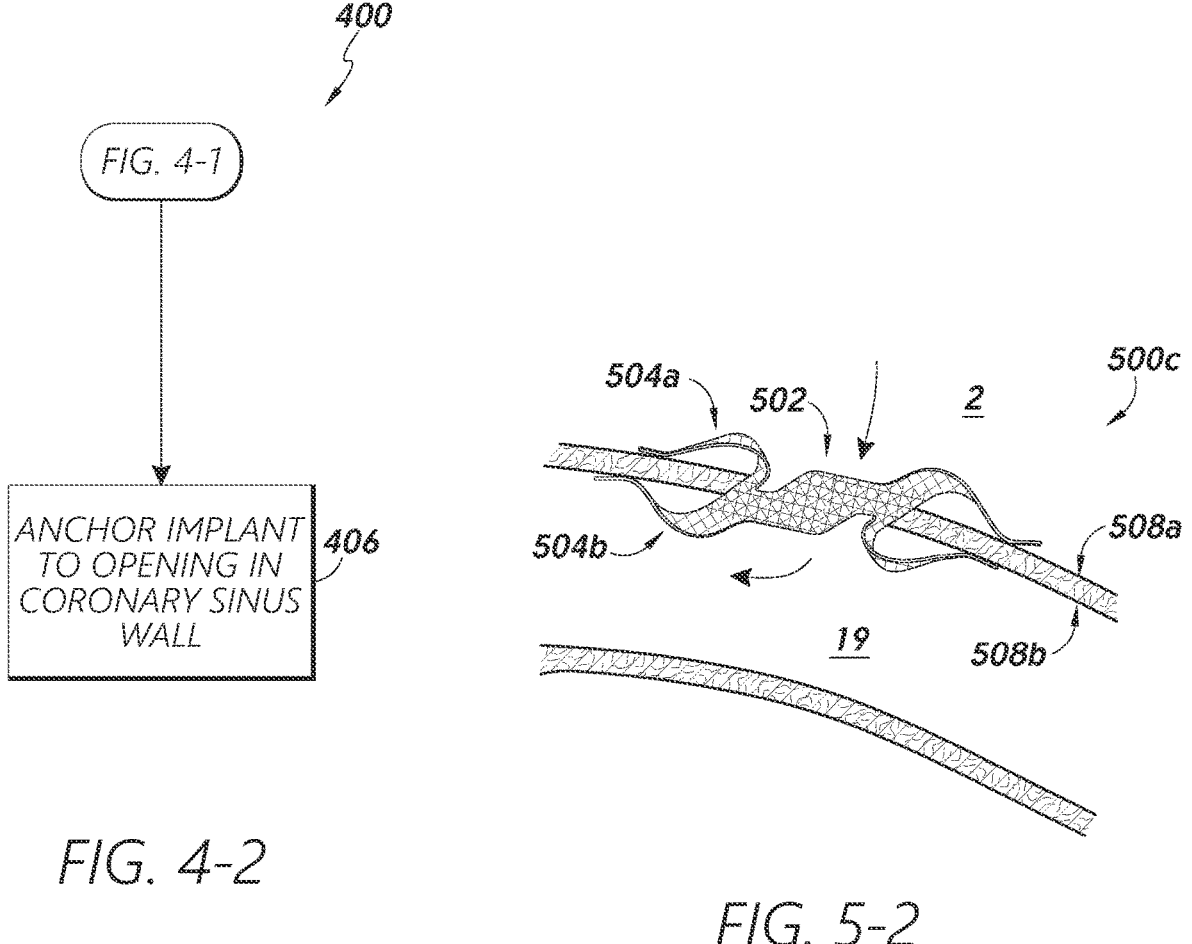
FIG. 4 (FIGS. 4-1 and 4-2) is a flow diagram illustrating a process for delivering and/or anchoring an implant to a treatment site in accordance with one or more embodiments of the present disclosure.
FIG. 5 (FIGS. 5-1 and 5-2) provides several images associated with the process of FIG. 4 to illustrate aspects of the process according to one or more implementations thereof.

FIG. 4 (FIGS. 4-1 and 4-2) is a flow diagram illustrating a process 400 for delivering and/or anchoring an implant to a treatment site in accordance with one or more embodiments of the present disclosure. FIG. 5 (FIGS. 5-1 and 5-2) provides several images associated with the process 400 of FIG. 4 to illustrate aspects of the process according to one or more implementations thereof.

At step 402, the process 400 involves delivering an implant 501 to a pathway within a body, as shown in image 500a of FIG. 5. For example, the implant 501 may be delivered into the coronary sinus 19 via the right atrium 5. The implant 501 may be at least partially compressed onto an outer surface of a catheter 16. In some embodiments, the implant 501 may be at least partially enclosed by a sheath and/or other covering during delivery (see, e.g., the sheath in FIGS. 9A and 9B) to prevent the implant 501 from expanding and/or otherwise impeding delivery to a target location within the body. In some embodiments, wires and/or other mechanisms may be used to hold the implant 501 in a collapsed and/or crimped form. In such embodiments, a sheath may not be needed to hold the implant 501 in the collapsed and/or crimped form.

The implant 501 may have a generally flexible structure such that the catheter 16 may be able to bend as needed to enter the coronary sinus 19 and/or other pathway with minimal restriction from the implant 501. In some embodiments, the catheter 16 may comprise and/or may be attached to an atraumatic tip 509 configured to dilate various pathways and/or otherwise guide the catheter 16 and/or implant 501 to a desired location. Moreover, a guidewire 511 and/or similar device may be delivered to guide the catheter and/or implant 501 to the target location. In some embodiments, an opening 513 in a tissue wall 508 (e.g., a wall of the coronary sinus 19) may be created during the implant 501 delivery process 400 and/or an earlier process. The opening 513 may be created in any of a variety of ways. One example method is the following.

Initially, the guidewire 511 may be advanced, for example, from the right atrium into the coronary sinus 19 through its ostium or opening. A catheter 16 may be advanced over the guidewire. The catheter 16 may be introduced into the body through a proximal end of an introducer sheath. An introducer sheath may provide access to the particular vascular pathway (e.g., jugular or subclavian vein) and may have a hemostatic valve therein. While holding the introducer sheath at a fixed location, the surgeon can manipulate the puncture catheter to the implant site. A puncture sheath having a puncture needle with a sharp tip may be advanced along a catheter 16 and punctured through the wall 508 into, for example, the left atrium 2. A puncture expander may be advanced along the guidewire and through the tissue wall 508 into the left atrium 2. The puncture expander may be, for example, an elongated inflatable balloon. The puncture expander may be inflated radially outward so as to widen the puncture through the tissue wall 508.

At block 404, the process 400 involves passing the implant 501 at least partially through and/or to the opening 513 in the tissue wall 508 (e.g., the coronary sinus 19), as shown in image 500*b* of FIG. 5. The guidewire 511 may be situated at least partially on a distal side of the tissue wall 508 (e.g., within the left atrium 2) to guide the atraumatic tip 509 and/or implant 501 at least partially to the distal side of the tissue wall 508. Delivering the implant 501 may involve displacing the implant 501 from the catheter 16 when the catheter 16 is delivered to the implant location. For example, when the implant 501 is at least partially situated at or near the opening 513, a sheath covering the implant 501 and/or one or more wires holding the implant 501 in place may be at least partially retracted to allow the implant 501 to expand and/or become displaced from the catheter 16. The implant 501 may be configured to at least partially bend with the catheter 16 into the opening 513.

When the implant 501 is exposed from the catheter 16, the implant 501 may at least partially expand and/or the anchoring arms 504 may at least partially bend. In some embodiments, the implant 501 may be expanded manually and/or may be configured to naturally expand upon being at least partially removed from the catheter 16. However, expansion of the implant 501 may be assisted at least in part. For example, the catheter 16 and/or another surgical tool may be used to press against and/or pull the implant 501 to move the implant 501 towards an expanded shape and/or position.

At block 406, the process 400 involves anchoring the implant 501 within the opening 513 of the tissue wall 508 of the coronary sinus 19 and/or other blood vessel, as shown in image 500*c* of FIG. 5. The implant 501 may comprise one or more anchoring arms 504 configured to pinch and/or otherwise from an attachment to the tissue wall 508. The implant 501 may be configured to be situated such that blood may flow through the central flow portion 502 of the implant 501 (e.g., from the left atrium 2 into the coronary sinus 19).

The implant 501 may include a central flow portion 502 configured to fit at least partially within the opening 513 in the tissue wall. The central flow portion 502 may be configured to extend along sides of the opening 513 to maintain the opening 513 and/or to prevent ingrowth of tissue. The central flow portion 502 may be configured to allow blood flow through the implant 501. In some embodiments, the anchoring arms 504 may be configured to continue extend from the central flow portion 502 and/or may be configured to maintain the opening 513. The central flow portion 502 and/or anchoring arms 504 may comprise a network and/or pattern of struts and/or cords configured to form any suitable pattern and/or shape allowing blood flow through the central flow portion 502 and/or anchoring arms 504.

In some embodiments, a first anchoring arm 504*a* may be configured to contact and/or attach to a first side 508*a* of the tissue wall 508 and/or a second anchoring arm 504*b* may be configured to contact and/or attach to a second side 508*b* of the tissue wall 508. The first anchoring arm 504*a* and the second anchoring arm 504*b* may be configured to establish a pincer grip on the tissue wall 508 by pressing simultaneously against the first side 508*a* of the tissue wall 508 and the second side 508*b* of the tissue wall 508, respectively.

The implant 501 may comprise two sets of anchoring arms 504, each configured to anchor to different portions of the tissue wall 508. For example, a first set of anchoring arms 504 (including the first anchoring arm 504*a* and the second anchoring arm 504*b*) may be configured to establish a pincer grasp on a first portion of the tissue wall 508 while a second set of anchoring arms may be configured to establish a pincer grasp on a second portion of the tissue wall 508.

In some embodiments, one or more anchoring arms 504 may be configured to penetrate and/or hook onto the tissue wall 508. For example, one or more anchoring arms 504 may comprise one or more hooks extending from the anchoring arms 504 configured to penetrate the tissue wall 508 to establish a more secure attachment to the tissue wall 508.

The one or more anchoring arms 504 may be configured to naturally bend towards the tissue wall 508 upon delivery at the opening 513 in the tissue wall 508. For example, when the implant 501 is removed from a delivery device (e.g., a catheter), the implant 501 may naturally assume the form shown in image 500*c*. In some embodiments, the implant 501 may be shape-set and/or may be at least partially composed of a shape-memory alloy (e.g., Nitinol). For example, the implant 501 may be shape-set such that the first anchoring arm 504*a* and the second anchoring arm 504*b* may be configured to be pressed together and/or near each other such that when the tissue wall 508 is situated between the first anchoring arm 504*a* and the second anchoring arm 504*b*, the first anchoring arm 504*a* and the second anchoring arm 504*b* may be configured to securely pinch the tissue wall 508.

Figure 6:
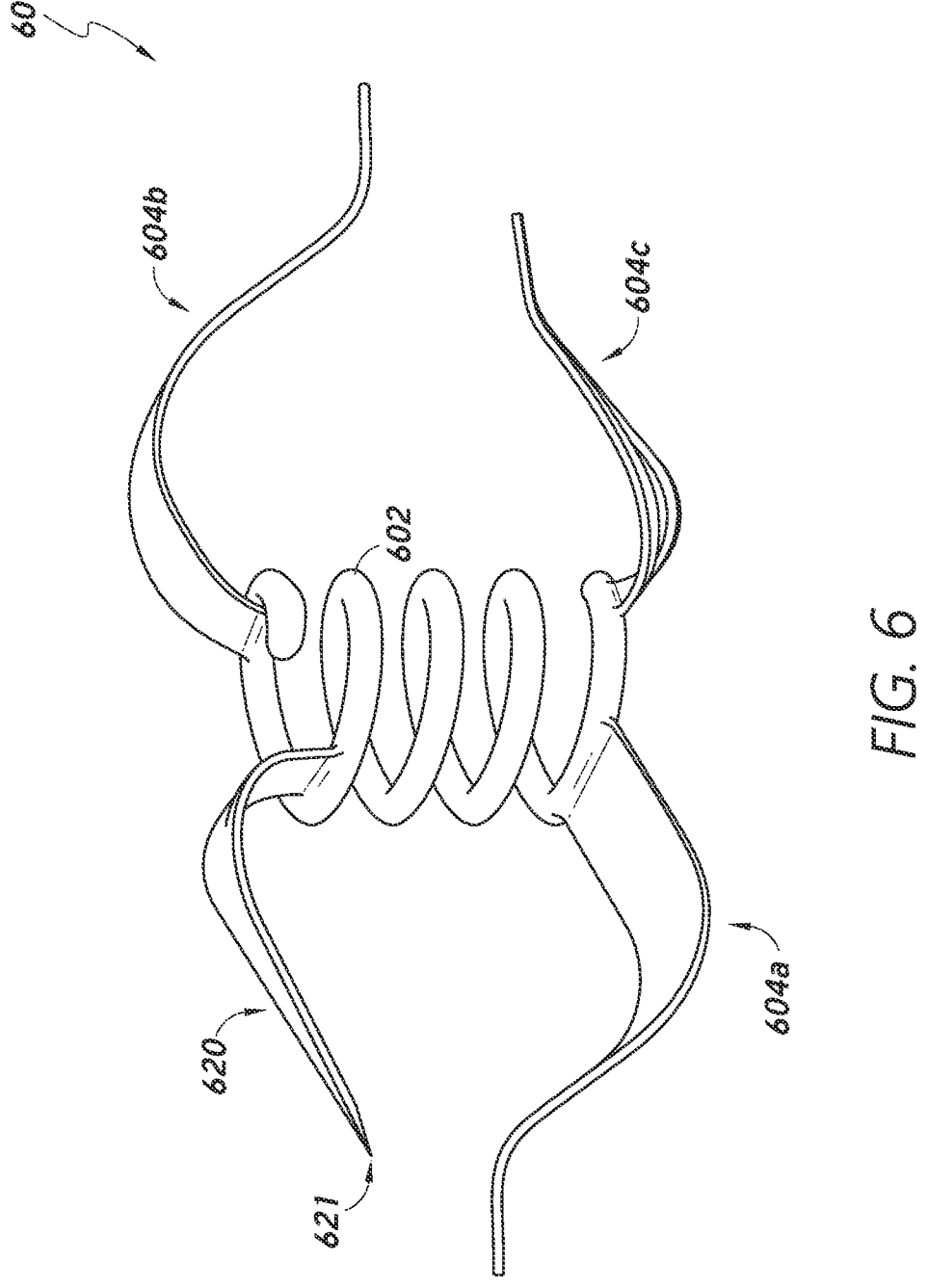
FIG. 6 illustrates another example shunt implant in accordance with embodiments of the present disclosure.

FIG. 6 illustrates another example shunt implant 601 in accordance with embodiments of the present disclosure. In some embodiments, the implant 601 may comprise a central flow portion 602 having a coiled and/or braided structure. For example, the central flow portion 602 may comprise one or more coiled cords, wires, and/or other elongate devices. The one or more cords may be formed in coils to form an inner lumen to allow blood flow through the central flow portion 602. While the implant 601 is shown in FIG. 6 having a coiled central flow portion 602, the implant 601 may additionally or alternatively comprise braided portions, similarly to the implant 300 of FIGS. 3A and 3B. Moreover, the implant 300 of FIGS. 3A and 3B may additionally or alternatively comprise coiled portions, similarly to the implant 601 of FIG. 6.

In some embodiments, the implant 601 may comprise a puncture element 620 configured to puncture through a tissue wall and/or to anchor to a tissue wall. The puncture element 620 may advantageously allow for surgeons to deliver the implant 601 without having to deliver a separate puncture element (e.g., a needle) prior to delivering the implant 601. In other words, creating an opening in a tissue wall and delivering the implant 601 to the opening in the tissue wall may be performed as a single-step process without having to remove devices from the body prior to delivering the implant 601.

As shown in FIG. 6, the puncture element 620 may be configured to extend from the central flow portion 602. In some embodiments, the puncture element 620 and/or one or more anchoring arms 604 may be configured to extend from the central flow portion 602. For example, the puncture element 620 may replace an anchoring arm 604 and/or may be used in conjunction with one or more anchoring arms 604. The puncture element 620 may be configured to perform functions similarly to an anchoring arm 604. For example, the puncture element 620 may be configured to establish a pincer grasp on a tissue wall together with a first anchoring arm 604_a_. A second anchoring arm 604_b_ and/or third anchoring arm 604_c_ may be configured to establish a pincer grasp on a different portion of a tissue wall.

The puncture element 620 may have any of a variety of forms and/or structures. In some embodiments, the puncture element 620 may have a generally conical form with a pointed tip 621 at one end and increasing in diameter and/or width from the pointed tip 621 to the central flow portion 602. The puncture element 620 may additionally or alternatively have a generally cylindrical structure (e.g., similarly to a needle) and forming the pointed tip 621 at an end portion. In another example, the puncture element 620 may have a general flat structure and/or may increase in width from the pointed tip 621 to the central flow portion 602. The puncture element 620 may be configured to form an opening in a tissue wall having a suitable size to fit the crimped/compressed implant 601 and/or a catheter through the opening. Accordingly, the puncture element 620 may be configured to at least partially increase in width and/or diameter from the pointed tip to increase the size of the opening created by the puncture element 620. Following delivery through an opening in a tissue wall, the puncture element 620 may be configured to contact and/or at least partially penetrate a surface of a tissue wall to anchor the implant 601 at the opening. For example, the pointed tip 621 may be configured to establish a single point of contact at the tissue wall. By establishing a single point of contact at the tissue wall, the puncture element 620 may be configured to assist in anchoring the implant 601 to the tissue wall while also minimizing surface contact to minimize in-growth of tissue around the puncture element and/or at the central flow portion 602.

The implant 601 may have a generally flexible structure. While the implant 601 is shown having a coiled structure, the implant 601 may additionally or alternatively comprise braided and/or interweaving elements to provide a measure of flexibility to the implant 601. Moreover, the puncture element 620 may be composed of an at least partially flexible material (e.g., Nitinol and/or thin portions of stainless steel) to allow the puncture element 620 to at least partially bend during delivery to the target location.

Figures 1, 2, 7, 8:
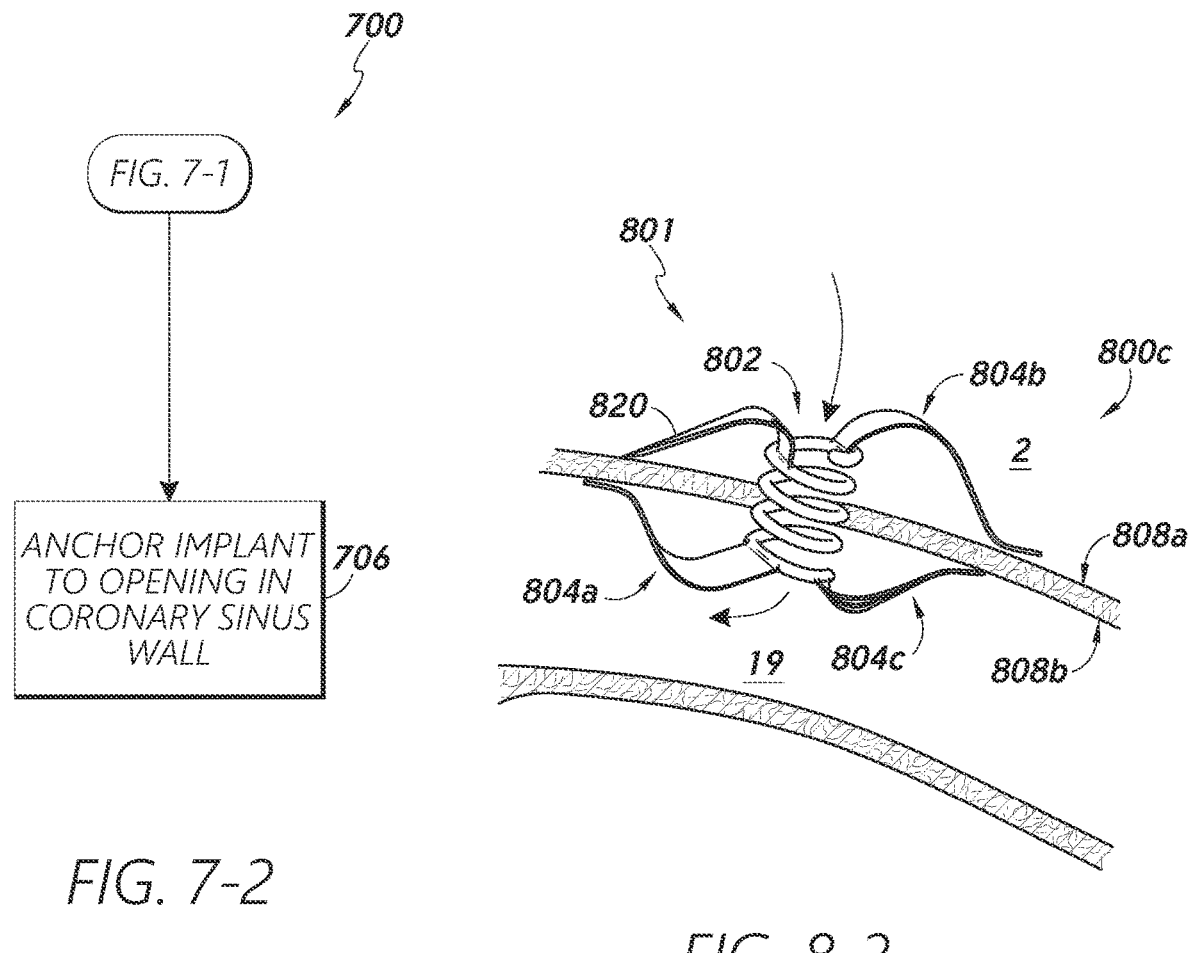
FIG. 7 (FIGS. 7-1 and 7-2) is a flow diagram illustrating a process for delivering and/or anchoring an implant to a treatment site in accordance with one or more embodiments of the present disclosure.
FIG. 8 (FIGS. 8-1 and 8-2) provides several images associated with the process of FIG. 7 to illustrate aspects of the process according to one or more implementations thereof.

FIG. 7 (FIGS. 7-1 and 7-2) is a flow diagram illustrating a process 700 for delivering and/or anchoring an implant to a treatment site in accordance with one or more embodiments of the present disclosure. FIG. 8 (FIGS. 8-1 and 8-2) provides several images associated with the process 700 of FIG. 7 to illustrate aspects of the process 700 according to one or more implementations thereof.

At step 702, the process 700 involves delivering an implant 801 to one or more flow pathways within a body, as shown in image 800_a_ of FIG. 8. For example, the implant 801 may be delivered into the coronary sinus 19 via the right atrium 5. The implant 801 may be at least partially compressed onto an outer surface of a catheter 16. While the implant 801 is shown in FIG. 8 having a coiled structure, the implant 801 may have any suitable structure, which may include one or more at least partially braided portions. In some embodiments, the implant 801 may be configured to be at least partially enclosed by a sheath and/or other covering during delivery (see, e.g., the sheath in FIGS. 9A and 9B) to prevent the implant 801 from expanding and/or otherwise impeding delivery to a target location within the body. In some embodiments, wires and/or other mechanisms may be used to hold the implant 801 in a collapsed and/or crimped form.

The implant 801 may have a generally flexible structure such that the catheter 16 may be able to bend as needed to enter the coronary sinus 19 and/or other pathway with minimal restriction from the implant 801. In some embodiments, the implant 801 may comprise at least one puncture element 820 configured to puncture and/or anchor to a tissue wall. The puncture element 820 may extend from a central portion and/or anchoring arm of the implant 801. In some embodiments, the puncture element 820 may be used in place of an anchoring arm and/or may be in combination with other anchoring arms. The puncture element 820 may be composed of any suitable material and/or combination of materials, which may include Nitinol and/or other metals. In some embodiments, the puncture element 820 may be configured to at least partially bend to allow the puncture element 820 and/or implant 801 to be more easily navigated to a target location (e.g., a wall of the coronary sinus 19).

In some embodiments, the puncture element 820 may have a generally tapered structure and/or may be configured to dilate various pathways and/or otherwise guide the catheter 16 and/or implant 801 to a desired location. The puncture element 820 may have a generally conical shape such that the puncture element 820 may be configured to create a circular-shaped opening 813 in the tissue wall 808. Moreover, a guidewire and/or similar device may be delivered to guide the catheter and/or implant 801 to the target location, as shown in image 800_b_ of FIG. 8.

At block 704, the process 700 involves passing the implant 801 at least partially through and/or to the opening 813 in the tissue wall 808 (e.g., the coronary sinus 19) created by the puncture element 820, as shown in image 800_b_ of FIG. 8. The puncture element 820 may be configured to pressed through the tissue wall to create the opening 813. In some embodiments, the puncture element 820 may be configured to create an opening 813 having a suitable size and/or width to allow the catheter 16 and/or implant 801 body to fit at least partially through the opening 813. The guidewire may be situated at least partially on a distal side of the tissue wall 808 (e.g., within the left atrium 2) to guide the catheter 16 and/or implant 801 at least partially to the distal side of the tissue wall 808. Delivering the implant 801 may involve displacing the implant 801 from the catheter 16 when the catheter 16 is delivered to the implant location. For example, when the implant 801 is at least partially situated at or near the opening 813, a sheath covering the implant 801 and/or one or more wires holding the implant 801 in place may be at least partially retracted to allow the implant 801 to expand and/or become displaced from the catheter 16. The implant 801 may be configured to at least partially bend with the catheter 16 into the opening 813.

When the implant 801 is removed from the catheter 16, the implant 801 may be configured to at least partially expand and/or the anchoring arms 804 may at least partially bend. In some embodiments, the implant 801 may be expanded manually and/or may be configured to naturally expand upon being at least partially removed from the catheter 16. However, expansion of the implant 801 may be assisted at least in part. For example, the catheter 16 and/or another surgical tool may be used to press against and/or pull the implant 801 to move the implant 801 towards an expanded shape and/or position.

At block 706, the process 700 involves anchoring the implant 801 within the opening 813 of the tissue wall 808, as shown in image 800c of FIG. 8. The implant 801 may comprise one or more anchoring arms 804 configured to pinch and/or otherwise from an attachment to the tissue wall 808. The implant 801 may be configured to be situated such that blood may flow through the central flow portion 802 of the implant 801 (e.g., from the left atrium 2 into the coronary sinus 19).

The implant 801 may include a central flow portion 802 configured to fit at least partially within the opening 813 in the tissue wall. The central flow portion 802 may be configured to extend along sides of the opening 813 to maintain the opening 813 and/or to prevent ingrowth of tissue. The central flow portion 802 may be configured to allow blood flow through the implant 801. In some embodiments, the anchoring arms 804 may be configured to continue extend from the central flow portion 802 and/or may be configured to maintain the opening 813.

In some embodiments, a first anchoring arm 804a may be configured to contact and/or attach to a second side 808b of the tissue wall 808 and/or the puncture element 820 may be configured to contact and/or attach to a first side 808a of the tissue wall 808. The first anchoring arm 804a and the puncture element 820 may be configured to establish a pincer grip on the tissue wall 808 by pressing simultaneously against the first side 808a of the tissue wall 808 and the second side 808b of the tissue wall 808, respectively. The implant 801 may comprise a set of anchoring arms (e.g., a second anchoring arm 804b and/or a third anchoring arm 804c) opposite the first anchoring arm 804a and the puncture element 820, each configured to anchor to different portions of the tissue wall 808.

In some embodiments, one or more anchoring arms 804 may be configured to penetrate and/or hook onto the tissue wall 808. For example, one or more anchoring arms 804 may comprise one or more hooks extending from the anchoring arms 804 configured to penetrate the tissue wall 808 to establish a more secure attachment to the tissue wall 808.

The one or more anchoring arms 804 may be configured to naturally bend towards the tissue wall 808 upon delivery at the opening 813 in the tissue wall 808. For example, when the implant 801 is removed from a delivery device (e.g., a catheter), the implant 801 may naturally assume the form shown in image 800c. In some embodiments, the implant 801 may be shape-set and/or may be at least partially composed of a shape-memory alloy (e.g., Nitinol). For example, the implant 801 may be shape-set such that the first anchoring arm 804a and the puncture element 820 may be configured to be pressed together and/or near each other such that when the tissue wall 808 is situated between the first anchoring arm 804a and the puncture element 820, the first anchoring arm 804a and the puncture element 820 may be configured to securely pinch the tissue wall 808.

In some embodiments, the puncture element 820 may be configured to establish a single point of contact with the tissue wall 808. For example, a pointed tip of the puncture element 820 may be configured to penetrate the tissue wall. In this way, the puncture element 820 may advantageously limit tissue growth on the puncture element 820 and/or at the implant 801 due to a relatively low amount of surface contact between the puncture element 820 and the tissue wall 808.

Figures 9A, 9B:
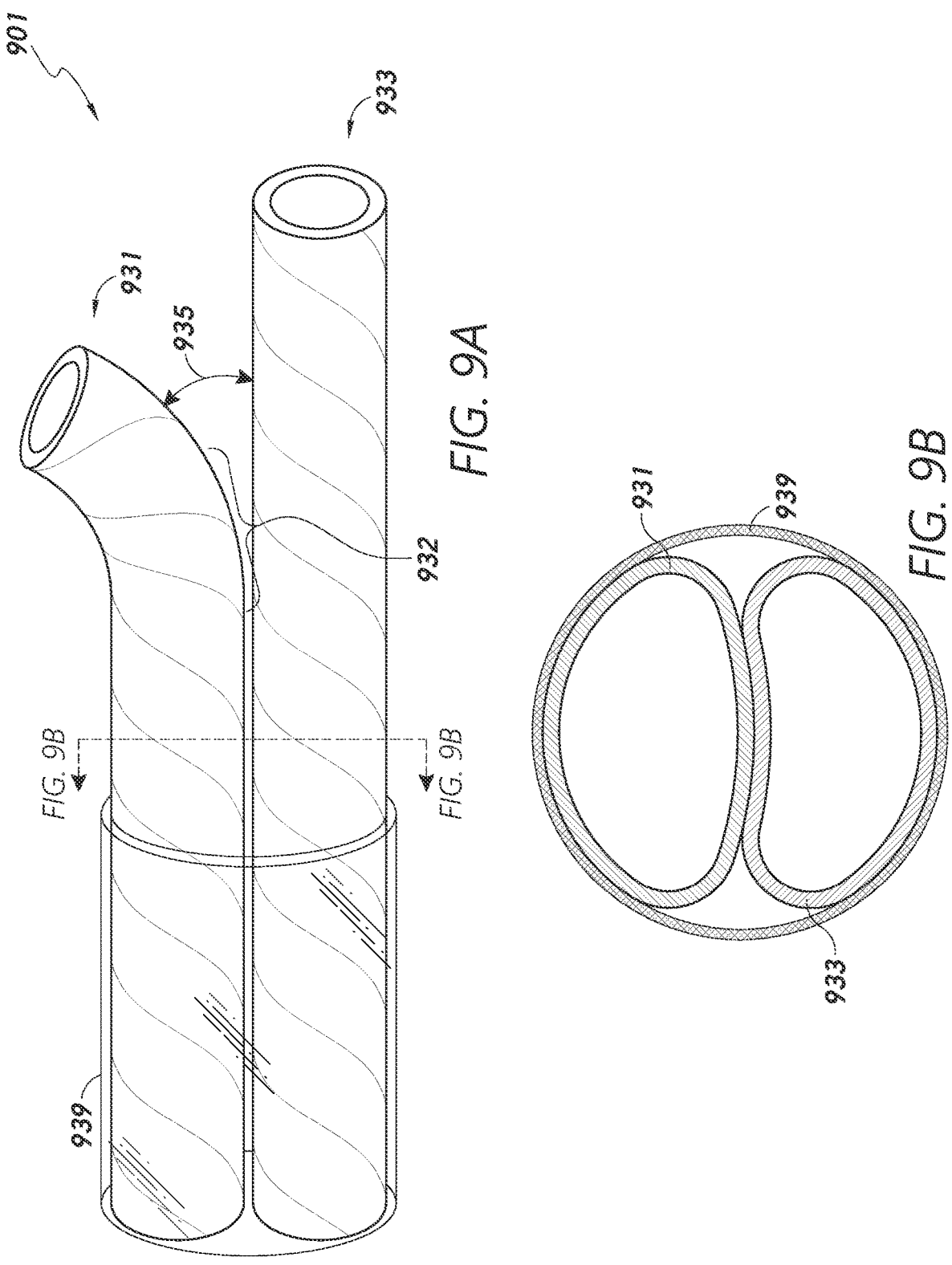
FIGS. 9A and 9B illustrate another example shunt implant in accordance with embodiments of the present disclosure.

FIGS. 9A and 9B illustrate another example shunt implant 901 in accordance with embodiments of the present disclosure. In some embodiments, the implant 901 may comprise a bi-lateral structure comprising two or more portions including a first portion 931 (e.g., first shunt) and a second portion 933 (e.g., second shunt). The first portion 931 and/or the second portion 933 may comprise generally tubular devices having inner lumens configured to receive and/or allow blood flow. In some embodiments, the first portion 931 and/or the second portion 933 may be at least partially fluid-tight and/or may be configured to allow blood flow through the tubular walls of the portions. For example, the first portion 931 and/or the second portion 933 may be formed at least partially of a braided and/or coiled network of cords and/or other devices providing gaps to allow blood flow.

The first portion 931 may be configured to allow shunting of blood flow from a first chamber (e.g., the left atrium) into a second chamber and/or blood pathway (e.g., the coronary sinus). Moreover, the first portion 931 may advantageously be configured to maintain an opening in a tissue wall. The second portion 933 may be configured to allow normal blood flow through a blood pathway (e.g., the coronary sinus). Moreover, the second portion 933 may be configured to at least partially prevent blood flow through the flow pathway from entering the first chamber. The first portion 931 and/or second portion 933 may have a generally tubular shape to allow the first portion 931 and/or second portion 933 to be able to bend and/or otherwise maintain a relatively high level of flexibility to simplify delivery of the implant 901 into the body.

In some embodiments, at least a portion of the first portion 931 and/or the second portion 933 may be at least partially fluid tight and/or may comprise one or more areas (e.g., a first area 932) at least partially composed of a material or materials configured to prevent blood flow through the one or more areas. For example, the first area 932 and/or other areas of the first portion 931 and/or the second portion 933 may be at least partially composed of a generally solid material that may not form gaps to thereby prevent blood flow through the first area 932. The first area 932 and/or other areas may be configured to be situated at least partially below an opening of a tissue wall and/or may be configured to redirect blood flow through the opening. For example, blood may flow generally perpendicularly through an opening due to blood pressure characteristics of the chambers on either side of the opening. Such blood flow may have a relatively high velocity and/or may be potentially damaging to various tissue walls, particularly if the blood flows directly into a tissue wall. The first portion 931 and/or the second portion 933 may advantageously be configured to prevent at least a portion of blood flow from flowing directly into a tissue wall by redirecting the blood along a flow pathway (e.g., along the coronary sinus) rather than directly into a tissue wall. For example, blood flow may be deflected and/or redirected by the first area 932 of the first portion 931.

The first portion 931 and/or the second portion 933 may be configured to be at least partially enclosed by a sheath 939 which may be configured to hold the first portion 931 and/or the second portion 933 together. The sheath may be at least partially composed of cloth and/or other material(s). FIG. 9B provides a cross-sectional view illustrating the first portion 931 and/or the second portion 933 within the sheath 939. In some embodiments, the sheath 939 may be configured to be extended entirely over the first portion 931 and/or the second portion 933. When the implant 901 is delivered to target location within a body, the sheath 939 may be configured to be at least partially retracted to expose at least a portion of the first portion 931 and/or the second portion 933. When the first portion 931 is exposed and/or removed from the sheath 939, the first portion 931 may be configured to at least partially bend to form an angle of separation 935 between the first portion 931 and the second portion 933. The angle of separation 935 may be any value between 0° and 90°.

In some embodiments, at least part of the first portion 931 may be configured to naturally bend away from the second portion 933. For example, the first portion 931 may be at least partially composed of a shape memory alloy (e.g., Nitinol) and/or may be shape-set to assume the bent form shown in FIG. 9A when removed from the sheath 939.

One or more anchoring elements may be attached to the first portion 931 and/or the second portion 933 to anchor the first portion 931 and/or the second portion 933 to a tissue wall. For example, one or more anchoring elements may extend from an end portion of the first portion 931 to allow the first portion 931 to anchor to a tissue wall after passing through an opening in the tissue wall.

The second portion 933 may be configured for retention of the first portion 931 within an opening of a tissue wall. For example, the second portion 933 may be configured to remain within a blood flow pathway while the first portion 931 extends away from the second portion 933 (e.g., generally perpendicularly from the second portion 933) to enter the opening. The second portion 933 may be sized and/or positioned such that the second portion 933 may be configured to press against walls of the blood flow pathway to prevent the first portion 931 from dropping and/or receding out of the opening after the first portion 931 has entered the opening.

Figure 10:
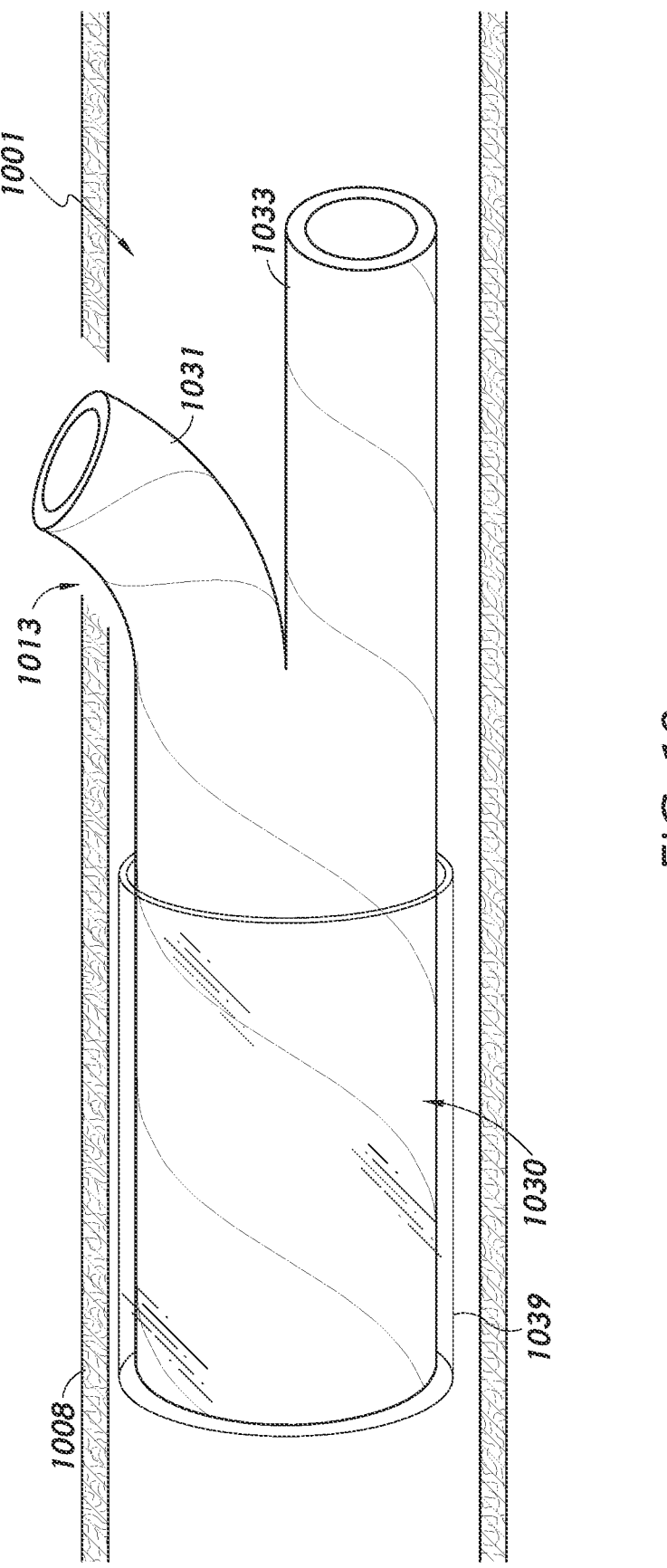
FIG. 10 illustrates another example shunt implant in accordance with embodiments of the present disclosure.

FIG. 10 illustrates another example shunt implant 1001 in accordance with embodiments of the present disclosure. The implant 1001 is shown in FIG. 10 within a blood flow pathway between tissue walls 1008. In some embodiments, an implant 1001 may comprise a first portion 1031 and/or a second portion 1033 configured to extend from a common base portion 1030.

The first portion 1031 and/or the second portion 1033 may comprise generally tubular devices having inner lumens configured to allow blood flow. In some embodiments, the first portion 1031 and/or the second portion 1033 may be at least partially fluid-tight and/or may be configured to allow blood flow through the tubular walls of the portions. For example, the first portion 1031 and/or the second portion 1033 may be formed at least partially of a braided and/or coiled network of cords and/or other devices providing gaps to allow blood flow. In some embodiments, at least a portion of the first portion 1031 and/or the second portion 1033 may be at least partially fluid tight and/or may comprise a one or more areas at least partially composed of a material or materials configured to prevent blood flow through the one or more areas (see, e.g., the first area 932 of FIGS. 9A and 9B).

The first portion 1031 and/or the second portion 1033 may be configured to be at least partially enclosed by a sheath 1039 which may be configured to hold the first portion 1031 and/or the second portion 1033 together. In some embodiments, the sheath 1039 may be configured to be extended entirely over the first portion 1031 and/or the second portion 1033. When the implant 1001 is delivered to target location within a body, the sheath 1039 may be configured to be at least partially retracted to expose at least a portion of the first portion 1031 and/or the second portion 1033. When the first portion 1031 is exposed and/or removed from the sheath 1039, the first portion 1031 may be configured to at least partially bend to form an angle of separation between the first portion 1031 and the second portion 1033. The angle of separation may be any value between 0° and 90°.

In some embodiments, the first portion 1031 may be configured to extend through an opening 1013 created in a tissue wall 1008. The opening 1013 may be formed prior to delivery of the implant 1001 as described previously herein. In some embodiments, the second portion 1033 and/or base portion 1030 may be sized and/or positioned to retain the first portion 1031 within the opening 1013 and/or to prevent the first portion 1031 from receding and/or dropping back completely into the blood flow pathway in which the second portion 1033 may be situated.

Figures 11, 12:
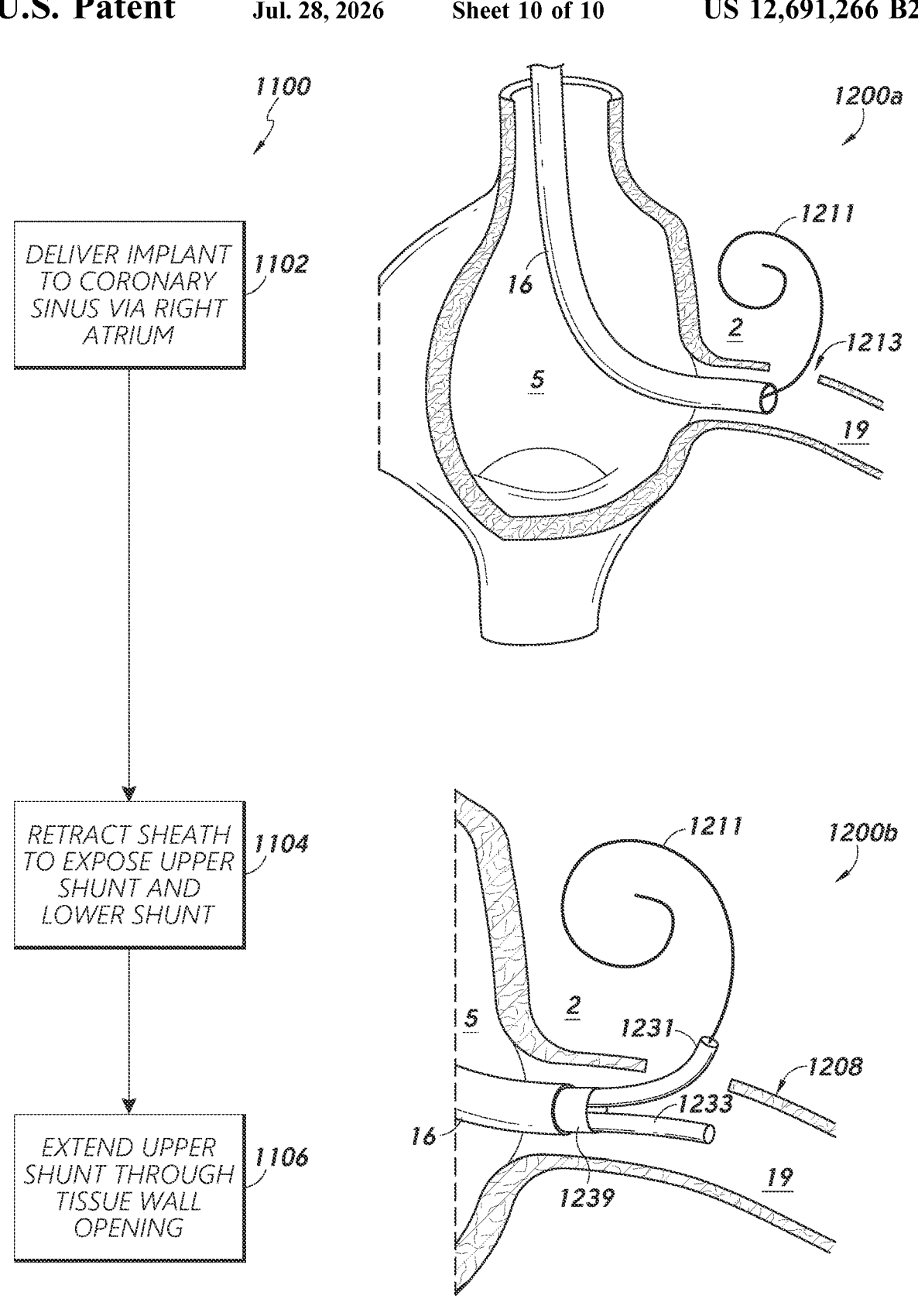
FIG. 11 is a flow diagram illustrating a process for delivering and/or anchoring an implant to a treatment site in accordance with one or more embodiments of the present disclosure.
FIG. 12 provides images associated with the process of FIG. 11 to illustrate aspects of the process according to one or more implementations thereof.

FIG. 11 is a flow diagram illustrating a process 1100 for delivering and/or anchoring an implant to a treatment site in accordance with one or more embodiments of the present disclosure. FIG. 12 provides several images associated with the process 1100 of FIG. 11 to illustrate aspects of the process 1100 according to one or more implementations thereof.

At step 1102, the process 1100 involves delivering an implant to one or more pathways within a body, as shown in image 1200a of FIG. 12. For example, the implant may be delivered into the coronary sinus 19 via the right atrium 5. The implant may be configured to be delivered via a catheter 16. In some embodiments, the implant may be configured to be at least partially enclosed by a sheath 1239 and/or other covering during delivery (see image 1200b of FIG. 12) to prevent the implant from expanding and/or otherwise impeding delivery to a target location within the body. In some embodiments, wires and/or other mechanisms may be used to hold the implant in a collapsed and/or crimped form. The implant may comprise one or more tubular portions (e.g., shunts) having lumens configured to receive blood flow and/or facilitate blood flow through and/or into the pathways. The implant may be delivered near (e.g., below) an opening 1213 of a tissue wall 1208. The opening 1213 may have been created during an earlier stage of a delivery process and/or a guidewire 1211 may have been delivered through the opening 1213 to guide the catheter 16.

At step 1104, the process 1100 involves retracting the sheath 1239 and/or catheter 16 to expose at least a portion of first (e.g., upper) shunt 1231 and/or second (e.g., lower) shunt 1233 and/or to allow the first shunt 1231 to at least partially separate from the second shunt 1233, as shown in image 1200b of FIG. 12. The sheath 1239 and/or catheter 16 may be configured to prevent expansion and/or separation of the first shunt 1231 and/or second shunt 1233. When the first shunt 1231 and/or second shunt 1233 are exposed and/or at least partially removed from the sheath 1239 and/or catheter 16, the first shunt 1231 and/or second shunt 1233 may be configured to assume a natural pre-determined form. For example, the first shunt 1231 and/or second shunt 1233 may be at least partially composed of one or more shape-memory materials (e.g., Nitinol) to cause the first shunt 1231 and/or second shunt 1233 to naturally gravitate towards a pre-determined shape. In some embodiments, at least a portion of the first shunt 1231 may be configured to naturally bend away from the second shunt 1233 when the first shunt 1231 is exposed.

At step 1106, the process 1100 involves extending the first shunt 1231 through the opening 1213 in the tissue wall 1208. For example, the first shunt 1231 may be configured to bend away from the second shunt 1233 to create some separation between the first shunt 1231 and the second shunt 1233. The first shunt 1231 may be configured to extend through an opening 1213 created in the tissue wall 1208. In some embodiments, the first shunt 1231 and/or the catheter 16 may be configured to track along the guidewire 1211 delivered previously into the body.

The second shunt 1233 may be configured to remain within the blood flow pathway (e.g., the coronary sinus 19) while the first shunt 1231 extends out of the blood flow pathway and/or into a chamber (e.g., the left atrium 2) on a distal side of the tissue wall 1208. In some embodiments, the second shunt 1233 may be configured to at least partially stabilize the first shunt 1231 and/or to prevent the first shunt 1231 from receding out of the opening 1213 in the tissue wall 1208. For example, the second shunt 1233 may be configured to press against one or more walls of the blood flow pathway to prevent the first shunt 1231 from dropping out of the opening 1213.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

Delivery systems as described herein may be used to position catheter tips and/or catheters to various areas of a human heart. For example, a catheter tip and/or catheter may be configured to pass from the right atrium into the coronary sinus. However, it will be understood that the description can refer or generally apply to positioning of catheter tips and/or catheters from a first body chamber or lumen into a second body chamber or lumen, where the catheter tips and/or catheters may be bent when positioned from the first body chamber or lumen into the second body chamber or lumen. A body chamber or lumen can refer to any one of a number of fluid channels, blood vessels, and/or organ chambers (e.g., heart chambers). Additionally, reference herein to "catheters," "tubes," "sheaths," "steerable sheaths," and/or "steerable catheters" can refer or apply generally to any type of elongate tubular delivery device comprising an inner lumen configured to slidably receive instrumentation, such as for positioning within an atrium or coronary sinus, including for example delivery catheters and/or cannulas. It will be understood that other types of medical implant devices and/or procedures can be delivered to the coronary sinus using a delivery system as described herein, including for example ablation procedures, drug delivery and/or placement of coronary sinus leads.

What is claimed is:

1. A delivery system comprising:
a catheter configured to be delivered through a blood flow pathway of a heart; and
an implant configured to:
maintain an opening in a tissue wall to allow blood flow through the opening and into the blood flow pathway; and
be delivered via the catheter, the implant being at least partially composed of a flexible material to allow the implant to bend with the catheter;
wherein the implant comprises a puncture element configured to puncture through a tissue wall to create the opening in the tissue wall.
2. The delivery system of claim 1, wherein the blood flow pathway is a coronary sinus and the opening creates a flow pathway between a left atrium and the coronary sinus.

3. The delivery system of claim 1, wherein the implant is configured to be crimped around an outer surface of the catheter.
4. The delivery system of claim 1, wherein the implant is at least partially composed of braided cords.
5. The delivery system of claim 1, wherein the implant is at least partially composed of a coiled cord.
6. The delivery system of claim 1, wherein the puncture element is further configured to anchor the implant to the tissue wall.
7. The delivery system of claim 6, wherein the implant further comprises an anchoring element, and the puncture element and the anchoring element are configured to anchor to opposing sides of the tissue wall.
8. The delivery system of claim 1, wherein the implant comprises a first tubular portion and a second tubular portion, and wherein:
the first tubular portion is configured to bend away from the second tubular portion to allow the first tubular portion to enter the opening in the tissue wall; and
the second tubular portion is configured to extend along the blood flow pathway and beyond the opening in the tissue wall.
9. The delivery system of claim 8, wherein the first tubular portion and the second tubular portion are separate devices.
10. The delivery system of claim 9, wherein the first tubular portion and the second tubular portion extend from a common base portion.
11. The delivery system of claim 10, wherein the first tubular portion is at least partially composed of a shape-memory material.
12. The delivery system of claim 11, further comprising a sheath configured to at least partially enclose the implant, and to retract to at least partially expose the implant and allow the implant to expand.
13. A method comprising:
delivering an implant enclosed at least partially by a sheath to a coronary sinus via a right atrium, wherein the implant is at least partially composed of braided or coiled cords to allow the implant to bend into the coronary sinus;
puncturing a tissue wall of the coronary sinus with the implant to create an opening between a left atrium and the coronary sinus;
retracting the sheath to expose the implant; and
anchoring the implant at the opening, wherein the implant is configured to maintain the opening.
14. The method of claim 13, wherein the implant comprises a puncture element, and puncturing the tissue wall is performed using the puncture element.
15. The method of claim 14, wherein anchoring the implant at the opening involves contacting the tissue wall with the puncture element.
16. The method of claim 14, wherein the puncture element is configured to establish a single point of contact with the tissue wall.
17. The method of claim 13, wherein the implant comprises a first tubular portion and a second tubular portion, and retracting the sheath allows the first tubular portion to bend away from the second tubular portion.
18. A medical implant comprising:
means for maintaining an opening through a tissue wall of a heart, the opening creating a blood flow path from a first chamber of a heart to a blood flow pathway of the heart, the means for maintaining the opening comprising a means for puncturing the tissue wall to create the opening, and the means for maintaining the opening configured to bend to facilitate delivery into the blood flow pathway and the first chamber; and means for anchoring to the tissue wall at the opening.

19. The medical implant of claim 18, wherein the blood flow pathway is a coronary sinus and the opening creates a flow pathway between a left atrium and the coronary sinus.

20. The medical implant of claim 18, wherein the means for maintaining the opening is configured to be crimped around an outer surface of a catheter.

21. The medical implant of claim 18, wherein the means for maintaining the opening is at least partially composed of braided cords.

22. The medical implant of claim 18, wherein the means for maintaining the opening is at least partially composed of a coiled cord.

23. The medical implant of claim 18, wherein the means for puncturing the tissue wall and the means for anchoring to the tissue wall are configured to anchor to opposing sides of the tissue wall.

24. The medical implant of claim 18, wherein the means for maintaining the opening comprises a first tubular portion and a second tubular portion, and wherein:

the first tubular portion is configured to bend away from the second tubular portion to allow the first tubular portion to enter the opening in the tissue wall; and the second tubular portion is configured to extend along the blood flow pathway and beyond the opening in the tissue wall.

25. The medical implant of claim 24, wherein the first tubular portion and the second tubular portion are separate devices.

26. The medical implant of claim 25, wherein the first tubular portion and the second tubular portion extend from a common base portion.

27. The medical implant of claim 26, wherein the first tubular portion is at least partially composed of a shape-memory material.

28. The medical implant of claim 27, further comprising a sheath configured to at least partially enclose the means for maintaining the opening, and to retract to at least partially expose the means for maintaining the opening and allow the means for maintaining the opening to expand.

29. The method of claim 13, wherein the implant is at least partially composed of braided cords.

30. The method of claim 13, wherein the implant is at least partially composed of a coiled cord.

31. The method of claim 14, wherein the implant further comprises an anchoring element, and the puncture element and the anchoring element are configured to anchor to opposing sides of the tissue wall.

32. The method of claim 17, wherein the first tubular portion and the second tubular portion are separate devices.

33. The method of claim 32, wherein the first tubular portion and the second tubular portion extend from a common base portion.

34. The method of claim 33, wherein the first tubular portion is at least partially composed of a shape-memory material.

\* \* \* \* \*